(12) United States Patent
Whitehurst

(10) Patent No.: US 7,003,352 B1
(45) Date of Patent: Feb. 21, 2006

(54) TREATMENT OF EPILEPSY BY BRAIN STIMULATION

(75) Inventor: Todd K. Whitehurst, Frazier Park, CA (US)

(73) Assignee: Advanced Bionics Corporation, Valencia, CA (US)

(*) Notice: Subject to any disclaimer, the term of this patent is extended or adjusted under 35 U.S.C. 154(b) by 213 days.

(21) Appl. No.: 10/428,743

(22) Filed: May 2, 2003

Related U.S. Application Data

(60) Provisional application No. 60/383,317, filed on May 24, 2002.

(51) Int. Cl.
    *A61N 1/18* (2006.01)
(52) U.S. Cl. .................................................. 607/45
(58) Field of Classification Search .............. 607/1, 607/2, 45
    See application file for complete search history.

(56) References Cited

U.S. PATENT DOCUMENTS

| | | |
|---|---|---|
| 3,850,161 A | 11/1974 | Liss |
| 3,993,046 A | 11/1976 | Fernandez et al. |
| 5,193,539 A | 3/1993 | Schulman et al. |
| 5,193,540 A | 3/1993 | Schulman et al. |
| 5,312,439 A | 5/1994 | Loeb |
| 5,349,962 A | 9/1994 | Lockard et al. |
| 5,713,923 A | 2/1998 | Ward et al. |
| 5,743,860 A | 4/1998 | Hively et al. |
| 5,752,979 A | 5/1998 | Benabid |
| 5,792,186 A | 8/1998 | Rise |
| 5,800,474 A | 9/1998 | Benabid et al. |
| 5,830,857 A | 11/1998 | Carnahan et al. |
| 5,857,978 A | 1/1999 | Hively et al. |
| 5,978,702 A | 11/1999 | Ward et al. |
| 5,995,868 A | 11/1999 | Dorfmeister et al. |
| 6,016,449 A | 1/2000 | Fischell et al. |
| 6,018,682 A | 1/2000 | Rise |
| 6,051,017 A | 4/2000 | Loeb et al. |
| 6,066,163 A | 5/2000 | John |
| 6,128,538 A | 10/2000 | Fischell et al. |
| 6,134,474 A | 10/2000 | Fischell et al. |
| 6,415,184 B1 | 7/2002 | Ishikawa et al. |
| 6,464,687 B1 | 10/2002 | Ishikawa et al. |
| 6,473,639 B1 | 10/2002 | Fischell et al. |

(Continued)

FOREIGN PATENT DOCUMENTS

WO   WO-98/37926 A1   2/1998

(Continued)

OTHER PUBLICATIONS

Bazil, et al., "Advances in the Medical Treatment of Epilepsy", Annu. Rev. Med., vol. 49, (1998), pp. 135-162.

(Continued)

*Primary Examiner*—Scott M. Getzow
(74) *Attorney, Agent, or Firm*—Laura Haburay Bishop; Peter K. Johnson; Bryant R. Gold

(57) ABSTRACT

Introducing one or more stimulating drugs to the brain and/or applying electrical stimulation to the brain is used to treat epilepsy. At least one implantable system control unit (SCU) produces electrical pulses delivered via electrodes implanted in the brain and/or drug infusion pulses delivered via a catheter implanted in the brain. The stimulation is delivered to targeted brain structures to adjust the activity of those structures. The small size of the SCUs of the invention allow SCU implantation directly and entirely within the skull and/or brain. Simplicity of the preferred systems and methods and compactness of the preferred system are enabled by the modest control parameter set of these SCU, which do not require or include a sensing feature.

19 Claims, 15 Drawing Sheets

U.S. PATENT DOCUMENTS

| | | | |
|---|---|---|---|
| 6,480,743 B1 | | 11/2002 | Kirkpatrick et al. |
| 6,788,975 B1 | * | 9/2004 | Whitehurst et al. ............ 607/45 |
| 2002/0072770 A1 | | 6/2002 | Pless |
| 2002/0161403 A1 | | 10/2002 | Meadows et al. |

FOREIGN PATENT DOCUMENTS

| | | |
|---|---|---|
| WO | WO-98/43700 A1 | 3/1998 |
| WO | WO-98/43701 A1 | 3/1998 |
| WO | WO-00/10455 A1 | 3/2000 |

OTHER PUBLICATIONS

Beart, et al., "Excitatory Amino Acid Projections to the Nucleus of the Solitary Tract in the Rat: a Retrograde Transport Study Utilizing D-[3H]Aspartate and [3H]Gaba", J Auton Nerv Syst, vol. 50(1), (Dec. 1994), pp. 109-122.

Cameron, et al., "Micromodular Implants to Provide Electrical Stimulation of Paralyzed Muscles and Limbs", IEEE Transactions on Biomedical Engineering, vol. 44, No. 9, (Sep. 1997), pp. 781-790.

Davis, et al., "Cerebellar Stimulation for Seizure Control: 17-year study", Stereotact Funct Neurosurg, vol. 58(1-4) (1992), pp. 200-208.

Fanselow, et al., "Reduction of Pentylenetetrazole-Induced Seizure Activity in Awake Rats by Seizure-Triggered Trigeminal Nerve Stimulation", J Neurosci, vol. 20(21), (Nov. 2000), pp. 8160-8168.

Heath, et al., "Feedback Loop Between Cerebellum and Septal-Hippocampal Sites: Its Role in Emotion and Epilepsy", Bilo Psychiatry, vol. 15(4), (Aug. 1980), pp. 541-556.

Hodaie, et al., "Chronic Anterior Thalamus Stimulation for Intractable Epilepsy," Epilepsia, vol. 43(6), (2002), pp. 603-608.

Hooper, et al., "A Prospective Study of Thalamic Deep Brain Stimulation for the Treatment of Movement Disorders in Multiple Sclerosis", British Journal of Neurosurgery, vol. 16, No. 2, (Apr. 1, 2002), pp. 102-109.

Jeanmonod, et al., "Low-Threshold Calcium Spike Bursts in the Human Thalamus: Common Physiopathology for Sensory, Motor and Limbic Positive Symptoms", Brain, vol. 119, (1996), pp. 363-375.

Krahl, et al., "Locus Coeruleus Lesions Suppress the Seizure-Attenuating Effects of Vagus Nerve Stimulation", Epilepsia, vol. 39(7), (Jul. 1998), pp. 709-714.

Lozano, et al., "Chronic Thalamic Anterior Nucleus Stimulation for Intractable Epilepsy." Epilepsia, vol. 41 Suppl. 7(2000), p. 168.

Menetrey, et al., "Spinal and Trigeminal Projections to the Nucleus of the Solitary Tract: a Possible Substrate for Somatovisceral and Viscerovisceral Reflex Activation", J Comp Neurol, vol. 255(3), (Jan. 1987), pp. 439-450.

Nomura, et al., "Trigeminal Primary Afferent Neurons Projecting Directly to the Solitary Nucleus in the Cat: a transganglionic and Retrograde Horseradish Peroxidase Study", Neurosci Lett, vol. 50(1-3), (Sep. 1984), pp. 257-262.

Shandra, et al., "Vliianie Nizkochastotnoi Elektricheskoi Stimuliatsii Zubchatogo ladra Mozzhenka na Ochagi Epilepticheskoi Aktivosti [Effect of Low-Frequency Electric Stimulation of the Dentate Nucleus of the Cerebellum on Foci of Epileptic Activity]," Patol Fiziol Eksp Ter, vol. 3, (May-Jun. 1989), pp. 24-28.

South, et al., "Substance P-Containing Trigeminal Sensory Neurons Project to the Nucleus of the Solitary Tract", Brain Res, vol. 372(2), (May 1986), pp. 283-289.

Van Laere, et al., "Vagus Nerve Stimulation Refractory Epilepsy: SPECT Activation Study", J Nucl Med, vol. 41(7), (Jul. 2000), pp. 1145-1154.

Velasco, et al., "Acute and Chronic Electrical Stimulation of the Centromedian Thalamic Nucleus: Modulation of Reticulo-Cortical Systems and Predictor Factors for Generalized Seizure Control", Arch Med Res, vol. 31(3), (May-Jun. 2000), pp. 305-315.

Velasco, et al., "Subacute and Chronic Electrical Stimulation of the Hippocampus on Intractable Temporal Lobe Seizures. Preliminary Report", Arch Med Res, vol. 31(3), (May 2000), pp. 316-328.

Walker, et al., "Regulation of Limbic Motor Seizures by GABA and Glutamate Transmission in Nucleus Tractus Solitarius", Epilepsia, vol. 40(8), (Aug. 1999), pp. 1051-1057.

Whitehurst, McGivern, and Kuzma inventors for AB-116U; U.S. Appl. No. 10/081,820; filed Feb. 19, 2002; entitled "Fully Implantable Miniature Neurostimulator for Vagus Nerve Stimulation".

Whitehurst and McGivern inventors for AB-134U; U.S. Appl. No. 10/224/021; filed Aug. 19, 2002; entitled Treatment of Movement Disorders by.

Whitehurst, McGivern, and McClure inventors for AB-205U; U.S. Appl. No. 10/428,744; filed May 2, 2003; entitled "Treatment of Movement Disorders by Brain Stimulation".

Whitehurst, McGivern, and Kuzma inventors for AB-210U; U.S. Appl. No. 10/057,115; filed Jan. 24, 2002; entitled "Fully Implantable Miniature Neurostimulator for Stimulation as a Therapy for Epilepsy".

* cited by examiner

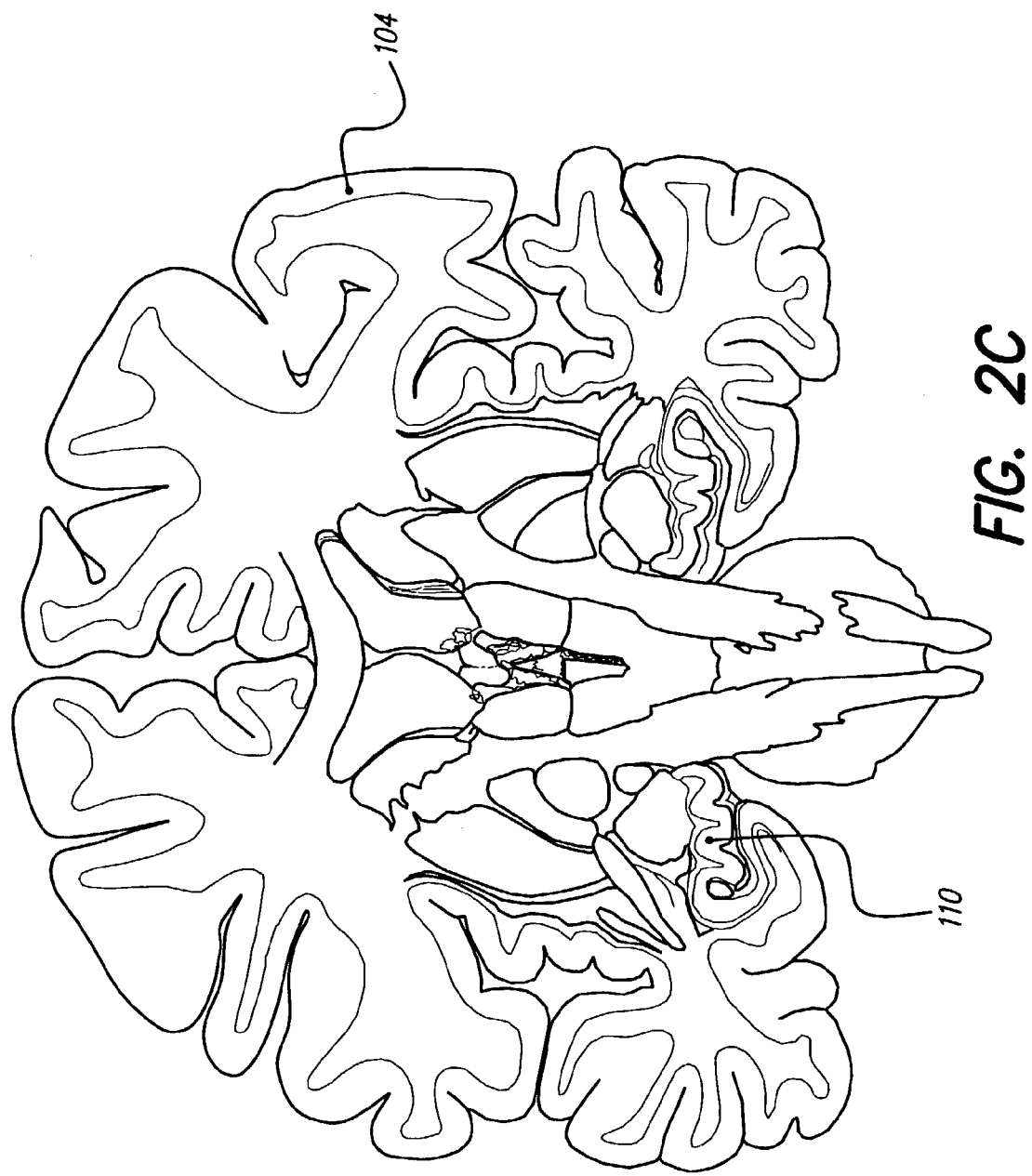

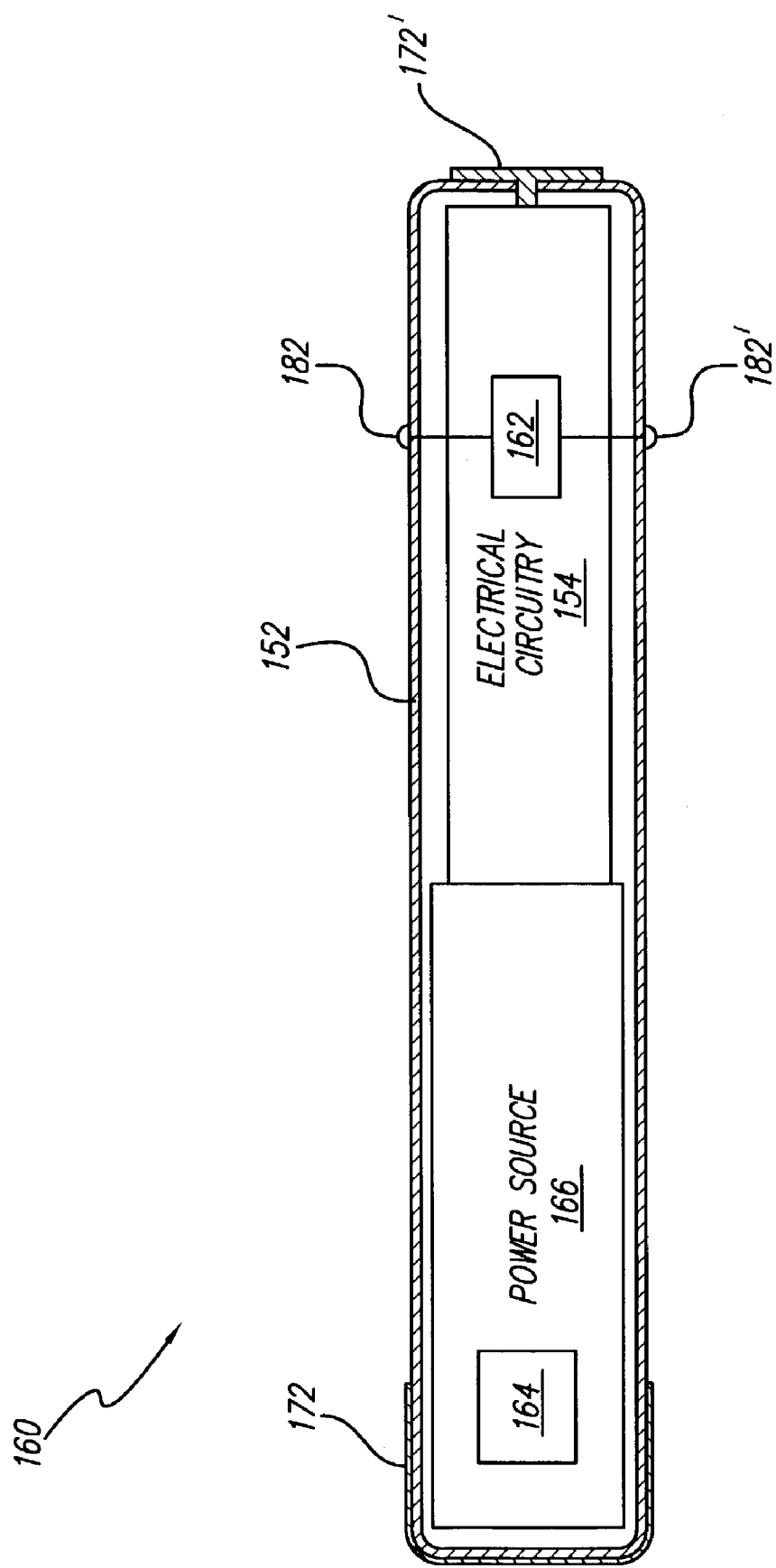

TREATMENT OF EPILEPSY BY BRAIN STIMULATION

The present application claims the benefit of U.S. Provisional Patent Application Ser. No. 60/383,317, filed May 24, 2002, which application is incorporated herein by reference in its entirety.

FIELD OF THE INVENTION

The present invention generally relates to implantable drug delivery and electrical stimulation systems and methods, and more particularly relates to utilizing one or more implantable devices to deliver electrical stimulation and/or one or more stimulating drugs to certain areas of the brain as a treatment for epilepsy.

BACKGROUND OF THE INVENTION

Epilepsy is characterized by a tendency to recurrent seizures that can lead to loss of awareness, loss of consciousness, and/or disturbances of movement, autonomic function, sensation (including vision, hearing and taste), mood, and/or mental function. Epilepsy afflicts 1–2% of the population in the developed world. The mean prevalence of active epilepsy (i.e., continuing seizures or the need for treatment) in developed and undeveloped countries combined is estimated to be 7 per 1,000 of the general population, or approximately 40 million people worldwide. Studies in developed countries suggest an annual incidence of epilepsy of approximately 50 per 100,000 of the general population. However, studies in developing countries suggest this figure is nearly double at 100 per 100,000.

The primary pathology of epilepsy is a synchronization of electrical activity between large numbers of brain neurons. Neurons "fire", i.e., transmit an electrical depolarization pulse down an axon(s), multiple times per second. While a group of adjacent neurons may normally demonstrate some correlation in their firing pattern, they normally do not all fire with exactly the same rate and exactly the same timing. However, during a seizure, a group of neurons in the brain demonstrate a highly synchronized firing pattern. This group may be localized, in which case it may be referred to as the seizure focus. In some types of epilepsy, the focus may remain fixed. In other types of epilepsy, the patient may have multiple fixed foci, and a seizure may arise from any of the foci. In still other types of epilepsy, a seizure may arise from a seemingly random location. Finally, in some types of epilepsy the seizure appears to arise from a majority of the brain all at once, i.e., with no focus. Seizures that arise from a focus may remain localized, in which case the symptoms of the seizure depend on the site of the focus. Seizures that arise from a focus may also spread to the majority of the brain, i.e., it may be initially focal but become secondarily generalized.

Epilepsy is often but not always the result of underlying brain disease. Any type of brain disease can cause epilepsy, but not all patients with the same brain pathology will develop epilepsy. The cause of epilepsy cannot be determined in a number of patients; however, the most commonly accepted theory posits that it is the result of an imbalance of certain chemicals in the brain, e.g., neurotransmitters. Children and adolescents are more likely to have epilepsy of unknown or genetic origin. The older the patient, the more likely it is that the cause is an underlying brain disease such as a brain tumor or cerebrovascular disease.

Trauma and brain infection can cause epilepsy at any age, and in particular, account for the higher incidence rate in developing countries. For example, in Latin America, neurocysticercosis (cysts on the brain caused by tapeworm infection) is a common cause of epilepsy; in Africa, AIDS and its related infections, malaria and meningitis, are common causes; in India, AIDS, neurocysticercosis, and tuberculosis are common causes. Febrile illness of any kind, whether or not it involves the brain, can trigger seizures in vulnerable young children, which seizures are called febrile convulsions. About 5% of such children go on to develop epilepsy later in life. Furthermore, for any brain disease, only a proportion of sufferers will experience seizures as a symptom of that disease. It is therefore suspected that those who do experience such symptomatic seizures are more vulnerable for similar biochemical/neurotransmitter reasons.

A number of U.S. patents have addressed using electrical and/or drug stimulation to increase and/or decrease excitement of various brain structures to treat epilepsy. For instance, U.S. Pat. Nos. 5,713,923 and 5,978,702 teach decreasing excitement/activity (or increasing inhibition) of the seizure focus, the globus pallidus interna (GPi), the substantia nigra reticulata (SNr), the anterior thalamic nucleus, the subthalamic nucleus (STN), and the neostriatum and increasing excitement/activity (or decreasing inhibition) of the ventrolateral (VL) thalamus, stiatopallidal fiber pathway, neostratium, the globus pallidus externa (GPe), and the GPe to STN fiber pathway. U.S. Pat. Nos. 5,800,474 and 5,752,979 teach blocking STN activity to reduce excitement of the SNr; the later does this by increasing GPe activity.

While these various treatment locations, methods, and systems exist, the inventors believe that enhanced systems, alternative locations, and modified methods will lead to improved treatment of epilepsy.

BRIEF SUMMARY OF THE INVENTION

The invention disclosed and claimed herein provides systems and methods for introducing one or more stimulating drugs and/or applying electrical stimulation to one or more areas of the brain for treating epilepsy or preventing or aborting a seizure. Treatment locations include the nucleus tractus solitarius (NTS).

The treatment provided by the invention may be carried out by one or more system control units (SCUs) that apply electrical stimulation and/or one or more stimulating drugs to one or more predetermined sites in the brain. In some forms of an SCU, one or more electrodes are surgically implanted to provide electrical stimulation from an implantable signal/pulse generator (IPG) and/or one or more infusion outlets and/or catheters are surgically implanted to infuse drug(s) from an implantable pump. In other forms of an SCU, a miniature implantable neurostimulator (a.k.a., a microstimulator), such as a Bionic Neuron (also referred to as a BION® microstimulator), is implanted.

In some configurations, the SCU is implanted in a surgically-created shallow depression or opening in the skull, such as in the temporal, parietal, or frontal bone. In some such configurations, one or more electrode leads and/or catheters attached to the SCU run subcutaneously to an opening in the skull and pass through the opening into or onto the dura, the brain parenchyma, and surrounding tissue. The SCUs programmed to produce electrical stimulation may provide either monopolar electrical stimulation, e.g., using the SCU case as an indifferent electrode, or bipolar electrical stimulation, e.g., using one of the electrodes of an electrode array as an indifferent electrode.

The SCU used with the present invention possesses one or more of the following properties, among other properties:

- at least one electrode for applying stimulating current to surrounding tissue and/or a pump and at least one outlet for delivering a drug or drugs to surrounding tissue;
- electronic and/or mechanical components encapsulated in a hermetic package made from biocompatible material(s);
- an electrical coil or other means of receiving energy and/or information inside the package, which receives power and/or data by inductive or radio-frequency (RF) coupling to a transmitting coil placed outside the body, thus avoiding the need for electrical leads to connect devices to a central implanted or external controller;
- means for receiving and/or transmitting signals via telemetry;
- means for receiving and/or storing electrical power within the SCU; and
- a form factor making the SCU implantable in a depression or opening in the skull and/or in the brain.

An SCU may operate independently, or in a coordinated manner with other implanted SCUs, other implanted devices, and/or with devices external to a patient's body.

The SCU preferably incorporates no means for sensing, which allows it to maintain its simplicity and thus its small size so that it can more readily be implanted entirely in the skull and/or brain. In addition, since the SCU does not incorporate feedback (i.e., operates in an open-loop), a significant amount of programming may be avoided. The relatively modest control parameter set allows for rapid programming, which programming may be done manually. Alternatively, the systems of the invention may include one or more sensors for sensing symptoms or conditions that may indicate a needed treatment.

BRIEF DESCRIPTION OF THE DRAWINGS

The above and other aspects of the present invention will be more apparent from the following more particular description thereof, presented in conjunction with the following drawings wherein:

FIGS. 2C–2F depict coronal section views of the brain of FIG. 2B;

FIGS. 3A, 3B, and 3C show some possible configurations of an implantable microstimulator of the present invention;

Corresponding reference characters indicate corresponding components throughout the several views of the drawings.

DETAILED DESCRIPTION OF THE INVENTION

Figure 1A:
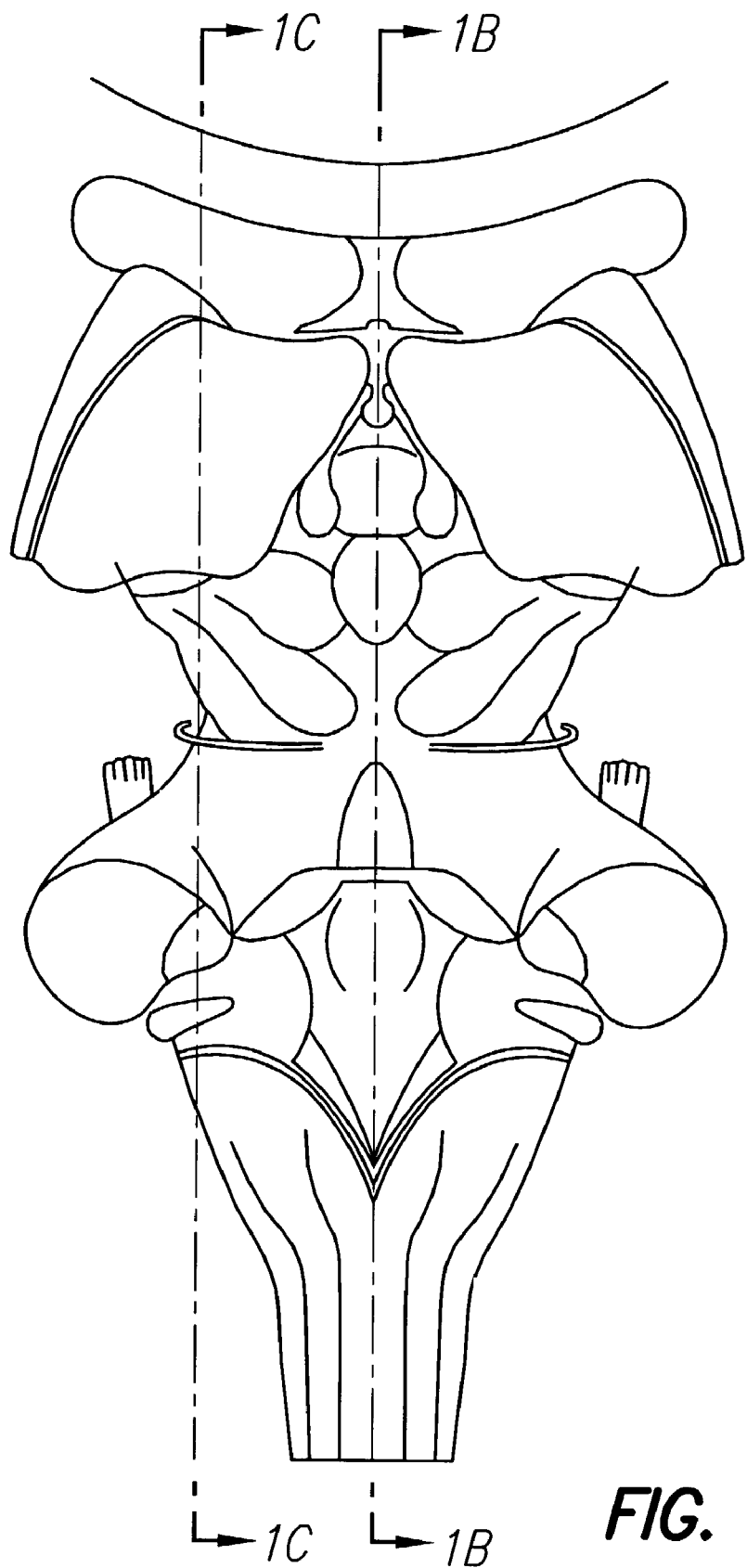
FIG. 1A depicts the dorsal surface of the brain stem.

The following description is of the best mode presently contemplated for carrying out the invention. This description is not to be taken in a limiting sense, but is made merely for the purpose of describing the general principles of the invention. The scope of the invention should be determined with reference to the claims.

Recent studies in both developed and developing countries have shown that up to 70% of newly diagnosed children and adults with epilepsy can be successfully treated (i.e., complete control of seizures for several years) with anti-epileptic drugs. After two to five years of successful treatment, drugs can be withdrawn in about 70% of children and 60% of adults without the patient experiencing relapses. However, up to 30% of patients are refractory to medication. There is evidence that the longer the history of epilepsy, the harder it is to control. The presence of an underlying brain disease typically results in a worse prognosis in terms of seizure control. Additionally, partial seizures, especially if associated with brain disease, are more difficult to control than generalized seizures.

Pharmacological agents for the treatment of epilepsy typically work by suppressing neural activity. For example, some epilepsy drugs appear to increase the threshold voltage at which a neuron may fire. These medications thus typically have sedative side effects. Other medications have significant negative side effects, including potential cognitive deficits.

Patients suffering from epilepsy may undergo surgery to remove a part of the brain in which the seizures are believed to arise, i.e., the seizure focus. However, in many patients a seizure focus cannot be identified, and in others the focus is in an area that cannot be removed without significant detrimental impact on the patient. For example, in temporal lobe epilepsy, patients may have a seizure focus in the hippocampi bilaterally. However, both hippocampi cannot be removed without devastating impacts on long-term memory. Other patients may have a seizure focus that lies adjacent to a critical area such as the speech center.

Vagus nerve stimulation (VNS) has been applied with partial success in patients with refractory epilepsy. In this procedure, an implantable pulse generator (IPG) is implanted in the patient's thorax, and an electrode lead is routed from the IPG to the left vagus nerve in the neck. Helix-shaped stimulation and indifferent electrodes are attached to the vagus nerve via an invasive surgical process that requires the carotid sheath to be fully exposed. Based on a number of studies, approximately 5% of patients undergoing VNS are seizure-free, and an additional 30–40% of patients have a greater than 50% reduction in seizure frequency.

In addition to this relatively low efficacy, VNS may lead to significant side effects. The vagus nerve provides parasympathetic innervation to the cardiac tissue, and thus VNS may lead to bradycardia, arrhythmia, or even graver cardiac side effects. In fact, VNS systems may only be used on the left vagus nerve, as the right vagus nerve contributes significantly more to cardiac innervation. Additionally, VNS may interfere with proper opening of the vocal cords, which has led to hoarseness and shortness of breath in a significant number of VNS patients.

The exact mechanism of action of seizure suppression of VNS is unknown. The nucleus of tractus solitarius (NTS; a.k.a., nucleus of the solitary tract) is a primary site at which vagal afferents terminate. Because afferent vagal nerve stimulation has been demonstrated to have anticonvulsant effects, it is likely that changes in synaptic transmission in the NTS can regulate seizure susceptibility. To demonstrate this, Walker, et al. ("Regulation of limbic motor seizures by GABA and glutamate transmission in nucleus tractus solitarius," Epilepsia, 1999 August) applied muscimol, an agonist of the inhibitory neurotransmitter GABA, to the NTS in a murine model of epilepsy. Muscimol applied to the NTS attenuated seizures in all seizure models tested, whereas muscimol applied to adjacent regions of NTS had no effect. Additionally, bicuculline methiodide, a GABA antagonist, injected into the NTS did not alter seizure responses. Finally, anticonvulsant effects were also obtained with application of lidocaine, a local anesthetic, into the NTS. Unilateral injections were sufficient to afford seizure protection. Walker, et al. concludes that inhibition of the NTS outputs enhances seizure resistance in the forebrain and provides a potential mechanism for the seizure protection obtained with vagal stimulation.

The NTS sends fibers bilaterally to the reticular formation and hypothalamus, which are important in the reflex control of cardiovascular, respiratory, and gastrointestinal functions. The NTS also provides input to the dorsal motor nucleus of the vagus, which enables the parasympathetic fibers of the vagus nerve to control these reflex responses. The NTS runs the entire length of the medulla oblongata, and the NTS (as well as the trigeminal nuclei) receives somatic sensory input from all cranial nerves, with much of its input coming from the vagus nerve.

Convincing evidence has been presented that a significant number of neurons in the trigeminal nerve project to the NTS. After applying horseradish peroxidase to peripheral branches of the trigeminal nerve in the cat, Nomura, et al found that branches of the trigeminal nerve (the lingual and pterygopalatine nerves) were found to contain fibers which ended ipsilaterally in the rostral portions of the NTS: massively in the medial and ventrolateral NTS, moderately in the intermediate and interstitial NTS, and sparsely in the ventral NTS. (The rostralmost part of the NTS was free from labeled terminals.) After injecting the enzyme into the NTS portions rostral to the area postrema, small neurons were scattered in the maxillary and mandibular divisions of the trigeminal ganglion. The authors concluded that trigeminal primary afferent neurons project directly to the NTS. [See Nomura, et al. "Trigeminal primary afferent neurons projecting directly to the solitary nucleus in the cat: a transganglionic and retrograde horseradish peroxidase study." *Neurosci Lett* 1984 Sep. 7; 50(1–3):257–62.] In another study, by staining for substance P immunoreactivity, South, et al found that Substance P-containing trigeminal sensory neurons project to the NTS. [See South, et al. "Substance P-containing trigeminal sensory neurons project to the nucleus of the solitary tract." *Brain Res* 1986 May 7; 372(2):283–9.]

The major brainstem nuclei that serve as the source for the trigeminal nerve are: the motor trigeminal nucleus, found in the midpons; the mesencephalic trigeminal nucleus located in the pons contains primary sensory neurons whose axons carry proprioceptive information from the muscles of mastication; the main (or primary) trigeminal sensory nucleus, the largest of the cranial nerve nuclei, which extends from the midbrain down to the second cervical segment of the spinal cord; and the spinal (or descending) trigeminal nucleus, which extends from the main trigeminal sensory nucleus to the dorsal gray of the spinal cord and contains secondary sensory neurons that process pain and temperature information.

Convincing evidence has also been reported that a significant number of neurons in the trigeminal nuclei project to the NTS. Menetrey, et al used the retrograde transport of a protein-gold complex to examine the distribution of spinal cord and trigeminal nucleus caudalis neurons that project to the NTS in the rat. [See Menetrey, et al. "Spinal and trigeminal projections to the nucleus of the solitary tract: a possible substrate for somatovisceral and viscerovisceral reflex activation." *J Comp Neurol* 1987 Jan. 15; 255(3): 439–50.] The authors found that retrogradely labeled cells were numerous in the superficial laminae of the trigeminal nucleus caudalis, through its rostrocaudal extent. Since the NTS is an important relay for visceral afferents from both the glossopharyngeal and vagus nerves, the authors suggest that the spinal and trigeminal neurons that project to the NTS may be part of a larger system that integrates somatic and visceral afferent inputs from wide areas of the body. The projections may underlie somatovisceral and/or viscerovisceral reflexes, perhaps with a significant afferent nociceptive component.

Beart, et al utilized microinfusion and retrograde transport of D-[3H]aspartate to identify excitatory afferents to the NTS. [See Beart, et al. "Excitatory amino acid projections to the nucleus of the solitary tract in the rat: a retrograde transport study utilizing D-[3H]aspartate and [3H]GABA." *J Auton Nerv Syst* 1994 Dec. 1; 50(1):109–22.] The authors found that the heaviest labeling was localized bilaterally in the trigeminal nucleus with cells extending through its subdivisions and the entire rostrocaudal axis.

The trigeminal nerve contributes a significant number of afferent fibers to the NTS. Additionally, trigeminal nerve afferents synapse on the trigeminal nucleus in the brainstem, and afferents from the trigeminal nucleus also project to the NTS. Thus, electrical stimulation of one or ore of the trigeminal nuclei may reasonably be expected to demonstrate efficacy in the treatment of patients with medically refractory epilepsy. In fact, Fanselow, et al. recently demonstrated that unilateral stimulation (via a chronically implanted nerve cuff electrode) of the infraorbital branch of the trigeminal nerve led to a reduction in electrographic seizure activity of up to 78%; the authors report that bilateral trigeminal stimulation was even more effective. [See Fanselow EE; Reid AP; Nicolelis M A. "Reduction of pentylenetetrazole-induced seizure activity in awake rats by seizure- triggered trigeminal nerve stimulation." *J Neurosci* 2000 Nov. 1; 20(21):8160–8.]

To determine the contribution of the locus coeruleus to the anti-epileptic effects of vagus nerve stimulation, Krahl, et al. chemically lesioned the locus coeruleus to determine if it is a critical structure involved in the anticonvulsant mechanisms of VNS (Krahl, et al. "Locus coeruleus lesions suppress the seizure-attenuating effects of vagus nerve stimulation." *Epilepsia* 1998 July; 39(7):709–14). Rats were chronically depleted of norepinephrine by a bilateral infusion of 6-hydroxydopamine (6-OHDA) into the locus coeruleus. (The locus coeruleus releases much of the norepinephrine neurotransmitter found in the brain.) Two weeks later, they were tested with maximal electroshock (MES) to assess VNS-induced seizure suppression. In another experiment, the locus coeruleus was acutely inactivated with lidocaine, and seizure suppression was tested in a similar fashion. VNS significantly reduced seizure severities of control rats. However, in animals with chronic or acute locus coeruleus lesions, VNS-induced seizure suppression was attenuated. This data indicates that the locus coeruleus is involved in the circuitry necessary for the anticonvulsant effects of VNS. Seizure suppression by VNS may therefore depend on the release of norepinephrine, a neuromodulator that has anticonvulsant effects. These data suggest that noradrenergic agonists might enhance VNS-induced seizure suppression.

The thalamus is believed to play a major role in some types of epilepsy by acting as a center for seizure onset or as a relay station in allowing a focal seizure to propagate. In a Single Positron Emission Computed Tomography (SPECT) study of patients with left-sided VNS systems, a consistent decrease of activity was found in the left thalamus caused by VNS. The authors concluded that left-sided VNS reduces seizure onset or propagation through inhibition of the thalamic relay center.

Thalamic relay neurons are essential in generating 3-Hz absence seizures and are believed to be involved in other types of epilepsy. Thalamic nuclei of some patients suffering from epilepsy display neuronal activities described as "low-threshold calcium spike bursts", which have been shown to be related to a state of membrane hyperpolarization of thalamic relay neurons. This thalamic rhythmicity is transmitted to the related cortex, thanks to thalamocortical resonant properties. In the cortex, an asymmetrical corticocortical inhibition (edge effect) at the junction between low and high frequency zones is proposed to be at the origin of a cortical activation of high frequency areas bordering low frequency ones.

The "thalamic relay" theory has led researchers recently to begin implanting deep brain stimulation (DBS) systems for stimulation of either the centromedian nucleus or the anterior nucleus of the thalamus, in order to treat medically refractory epilepsy patients. Unfortunately, the efficacy of this invasive procedure has thus far proven to be approximately the same as VNS.

In 1989, Shandra, et al. demonstrated with acute experiments on cats that seizure-related discharges were provoked by relatively low frequency (7–12 Hz) electrical stimulation of the ventrolateral nucleus of the thalamus (Shandra, et al. "Vliianie nizkochastotnoi elektricheskoi stimuliatsii zubchatogo iadra mozzhenka na ochagi epilepticheskoi aktivnosti [Effect of low-frequency electric stimulation of the dentate nucleus of the cerebellum on foci of epileptic activity]" *Patologicheskaia Fiziologiia I Eksperimental'naia Terapiia* 1989 May–Jun; (3):24–8). The authors further demonstrated that relatively low frequency (7–12 Hz) electrical stimulation of the dentate nucleus of the cerebellum induced seizure-related discharges in foci of epileptic activity produced in the brain cortex by application of penicillin solution. The authors additionally demonstrated that destruction of the ventrolateral nucleus of the thalamus abolished the effect of seizure discharge facilitation induced by stimulation of the dentate nucleus of the cerebellum. (Note that high frequency electrical stimulation of areas of the thalamus has been demonstrated to have inhibitory effects similar to a lesion.) In 1980, Heath, et al. demonstrated in monkeys that electrical stimulation through the vermis of the cerebellum inhibits epileptiform electroencephalographic activity at the cerebellum, septal region, and hippocampus (Heath, et al. "Feedback loop between cerebellum and septal-hippocampal sites: its role in emotion and epilepsy" *Biological Psychiatry* 1980 August; 15(4): 541–56).

In 1992, Davis, et al. followed up 32 seizure patients who had undergone chronic cerebellar stimulation (CCS) since 1974 (Davis et al. "Cerebellar stimulation for seizure control: 17-year study." *Stereotactic and Functional Neurosurgery* 1992; 58(1–4):200–8). The authors contacted 27 of these patients and found that nine (7 spastic, 2 epileptic) continued to use CCS for an average of 14.3 years (10–17 years). Six (67%) were seizure-free and three (33%) had a reduction of seizure frequency. Of two additional patients with spastic seizures who had used CCS for 13 years before their deaths, one had been seizure-free and the other had experienced a reduction. The remaining 16 patients (12 spastic, 4 epileptic) with nonfunctioning stimulators had used CCS for an average of 8.3 years (2–14 years); five (31%) continued to be seizure-free, seven (44%) had a reduction and four (25%) had no change or a slight increase. Overall, 23 (85%) patients benefitted from CCS. (Stimulation charge densities were 0.9–2.5 $\mu C/cm^2$/phase delivered at 10–180 pulses/sec to bilateral electrode pads on the superomedial cerebellar cortex.)

Direct electrical stimulation of the seizure focus may also be effective in the treatment of epilepsy. Velasco, et al. applied such therapy in patients with temporal lobe epilepsy (Velasco et al. "Subacute and chronic electrical stimulation of the hippocampus on intractable temporal lobe seizures. Preliminary report." *Archives of Medical Research* 2000 May; 31(3):316–28). In each patient, depth electrodes were implanted in the hippocampus for purposes of verifying that the seizure focus was in or near the hippocampus. While the electrodes were implanted, electrical stimulation was applied for several weeks or months to the electrode(s) near the seizure focus. Most patients experienced a significant decrease in the number of daily seizures while such electrical stimulation was applied. Subsequent to verification of the location of the seizure focus, a portion of the temporal lobe containing the seizure focus was removed from most of these patients. Histopathology of the stimulated areas (i.e., areas near the electrodes) demonstrated no significant detrimental effects, and neuropsychological testing suggested only positive changes in memory due to stimulation.

As noted above, high frequency electrical stimulation has been as efficacious as a lesion in the same area, presumably by inhibiting neural activity in the area. Such inhibition may underlie the seizure reduction observed in direct stimulation of the seizure focus. Alternatively, neurostimulation at relatively lower frequencies may somehow activate and/or "reprogram" local neural tissue, leading to reduced seizure activity. In contrast to ablation surgery, chronic electrical stimulation is reversible. Additionally, stimulation parameters may be adjusted to minimize side effects while maintaining efficacy; such "fine tuning" is unavailable when producing a lesion.

An implantable chronic stimulation device for DBS is commercially available and similar systems are under development. However, the current implant procedure is highly invasive, and the surgery for placement of the available system requires essentially an entire day. These systems require the power source and stimulation electronics to be implanted far from the electrodes, generally in the chest or elsewhere in the trunk of the body. These bulky systems therefore require extensive invasive surgery for implantation, and breakage of the long leads is highly likely.

For instance, the system manufactured by Medtronic, Inc. of Minneapolis, Minn. has several problems that make it an unacceptable option for some patients. It requires a significant surgical procedure for implantation, as the implantable pulse generator (IPG), a major component of the system containing the stimulation electronics and power source, is implanted in the thorax and connected via a subcutaneous tunnel to an electrode through the chest, neck and head into the brain. The IPG is also bulky, which may produce an unsightly bulge at the implant site (e.g., the chest), especially for thin patients. Additionally, the system is powered by a primary battery, which lasts only 3–4 years under normal operation. When the battery ceases to provide sufficient energy to adequately power the system, the patient must undergo an additional surgery in order to replace the IPG.

Figure 1B:
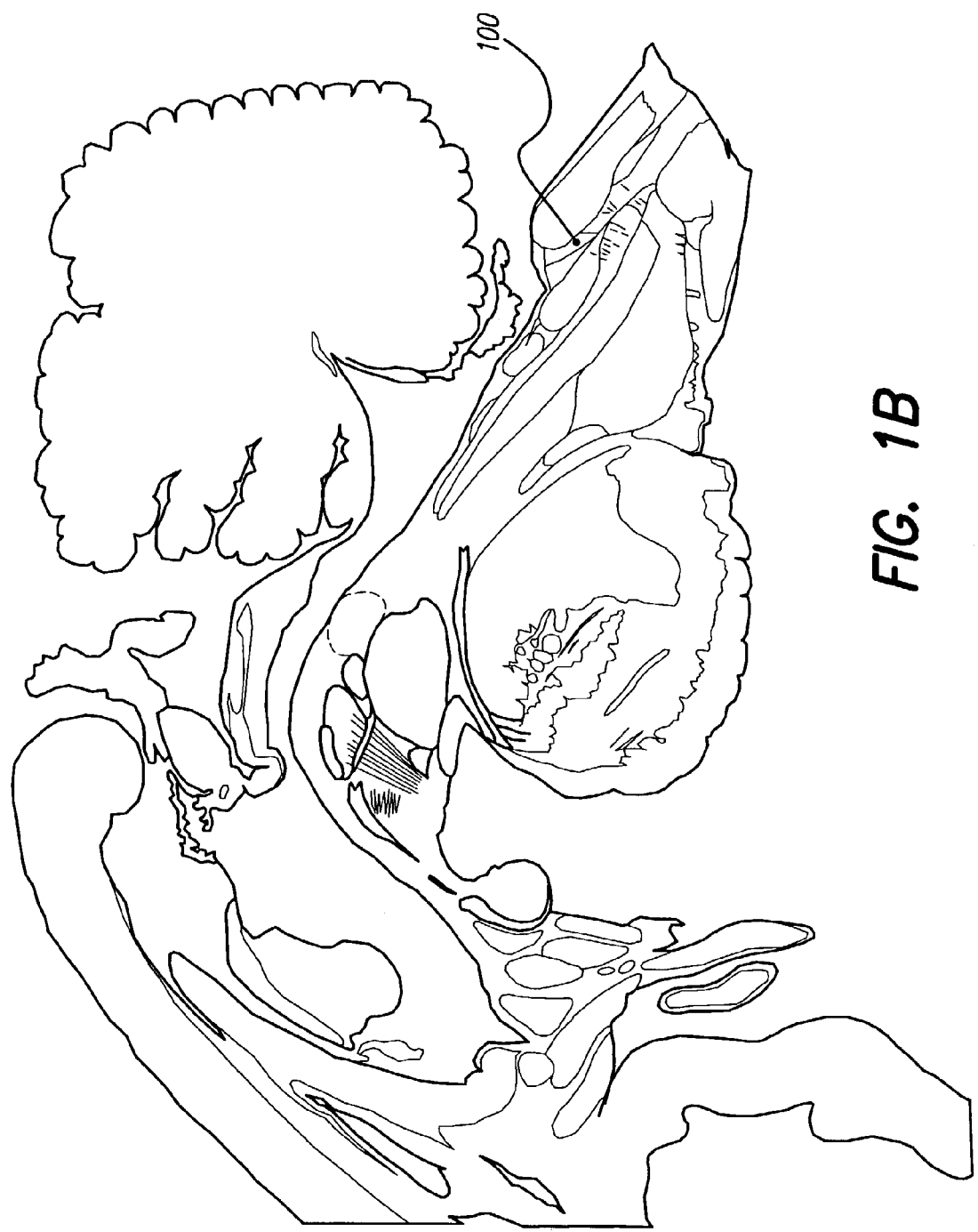
FIGS. 1B and 1C are section views through the brain stem depicted in FIG. 1A.
Figure 1C:
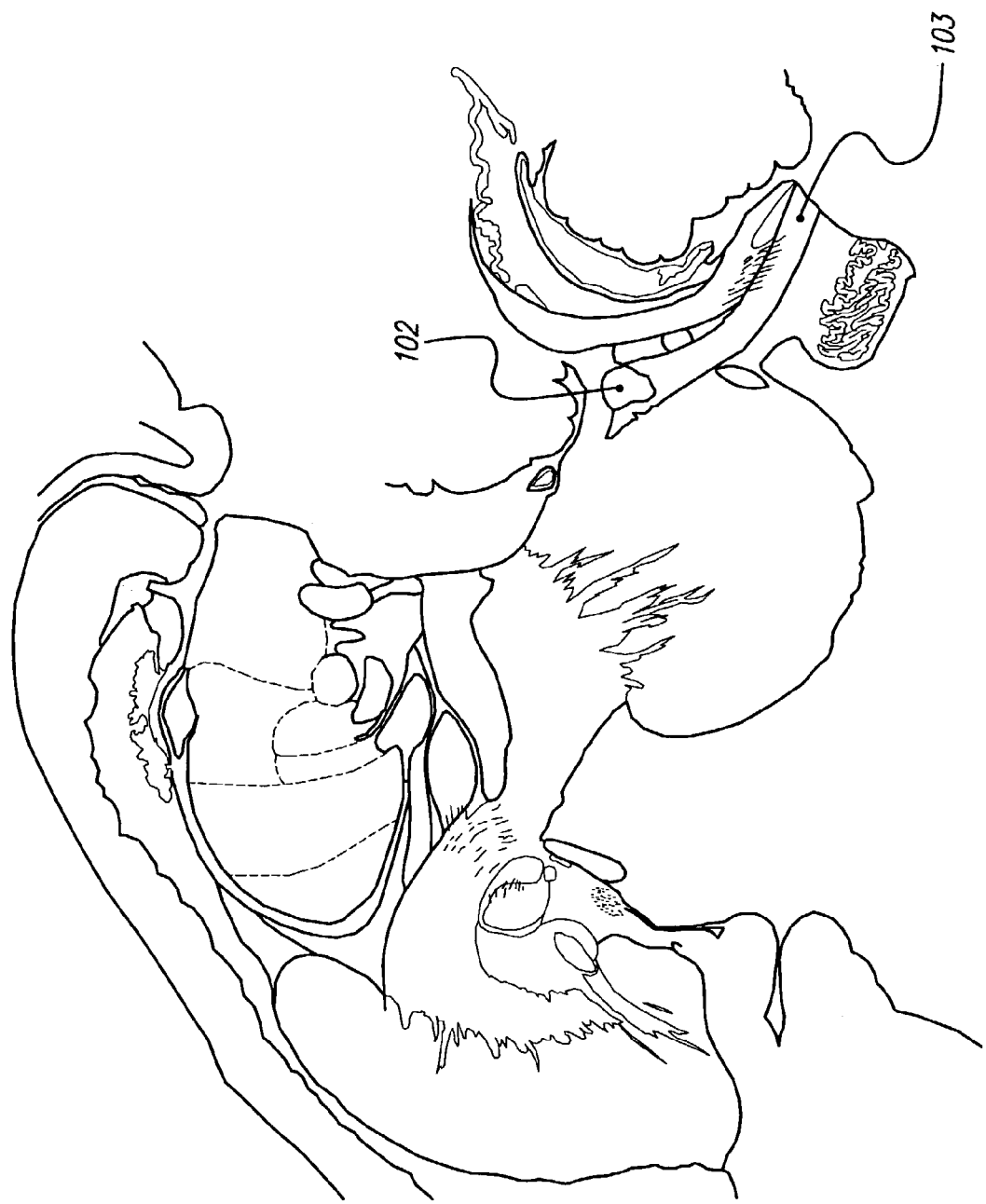
Figure 2A:
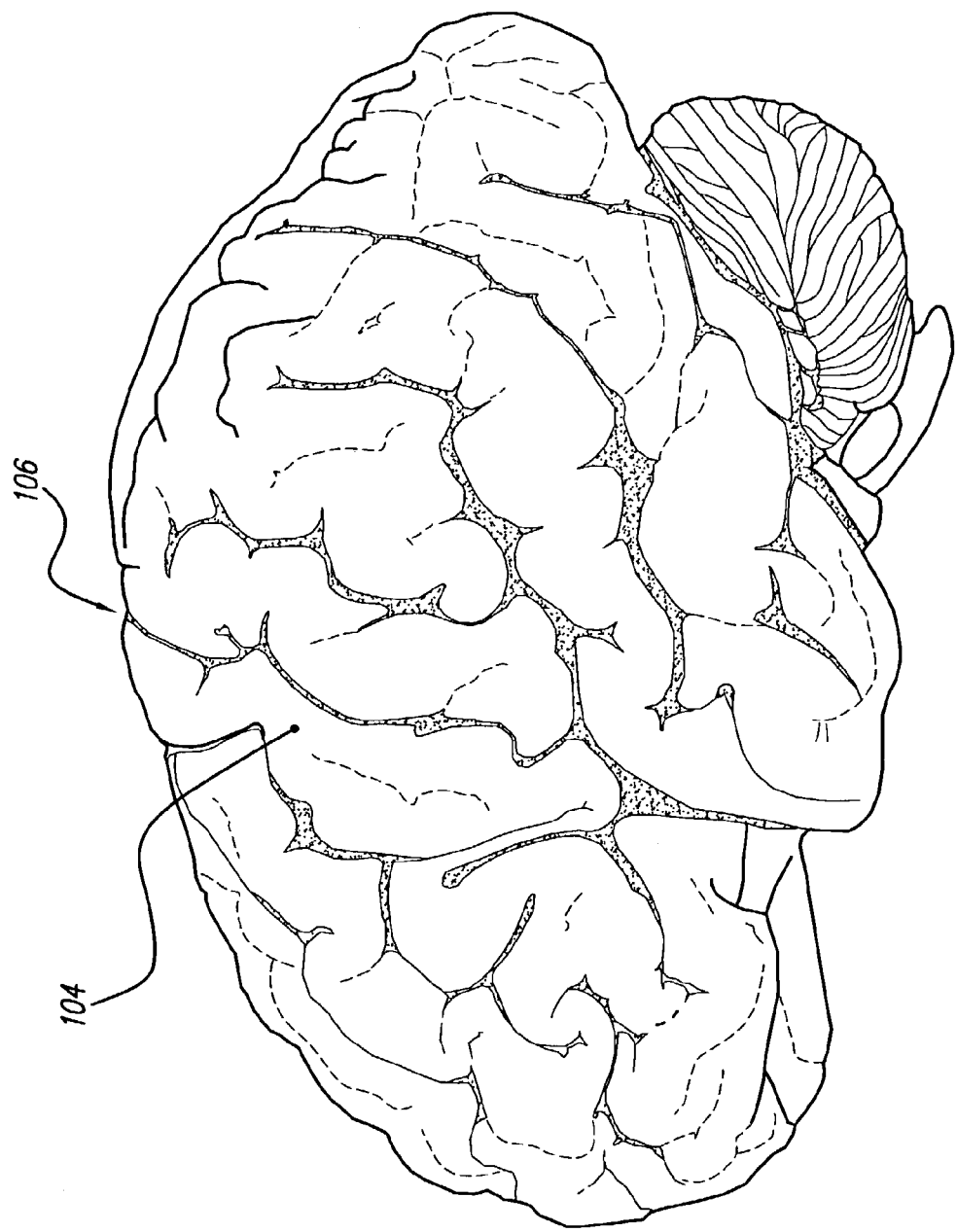
FIG. 2A depicts the lateral surface of the brain.
Figure 2B:
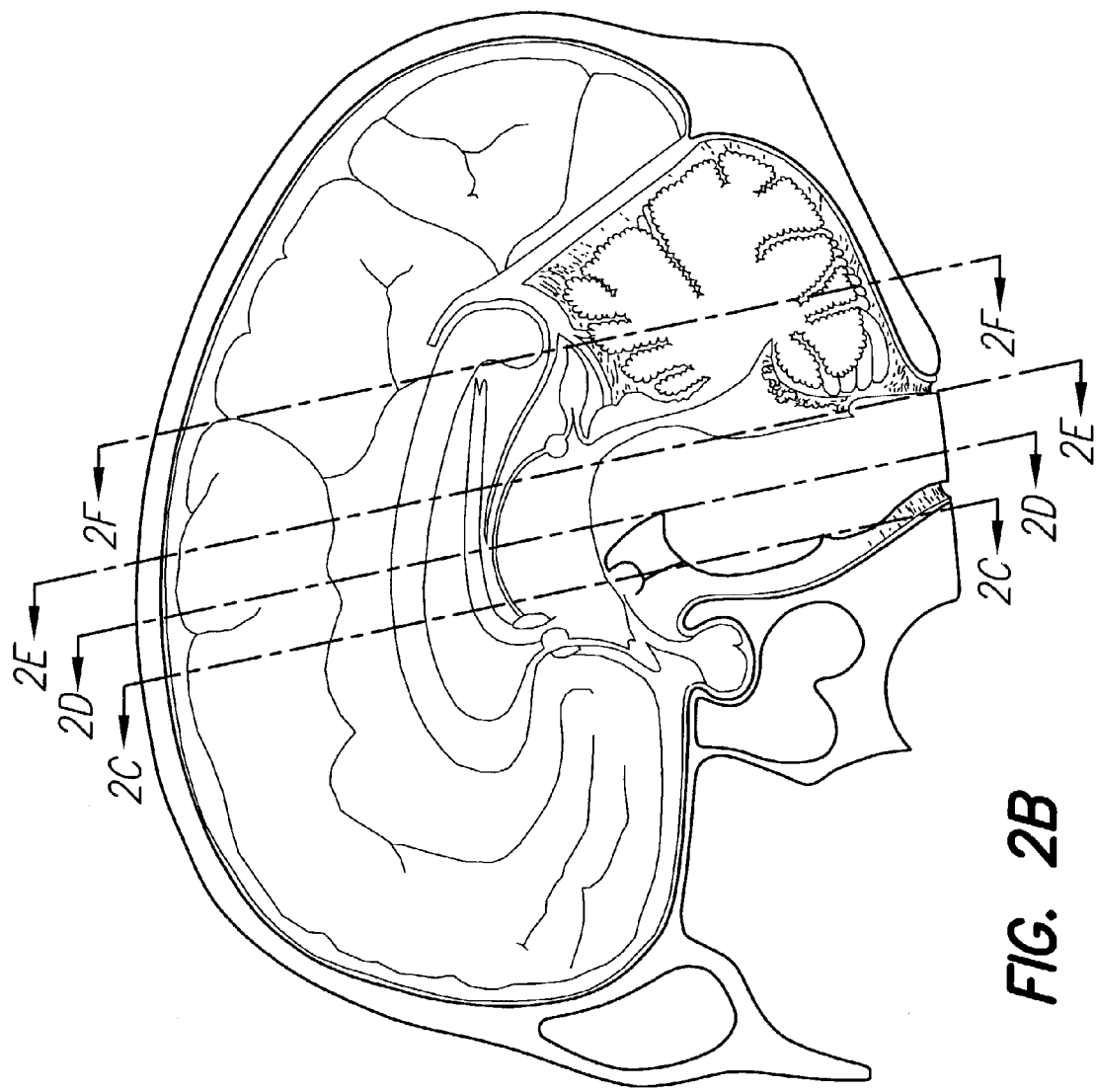
FIG. 2B depicts the medial surface of the head.
Figure 2D:
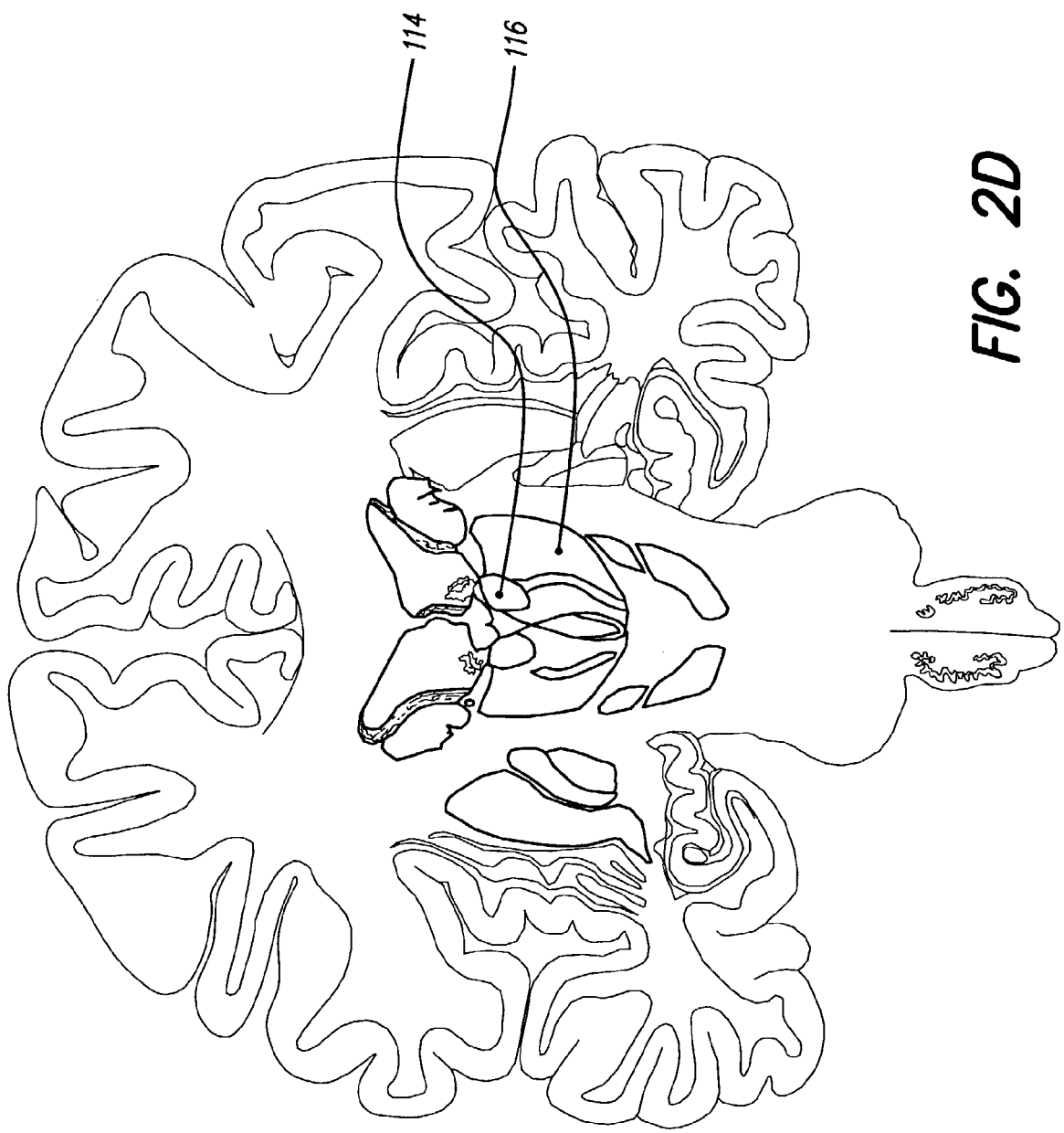
Figure 2E:
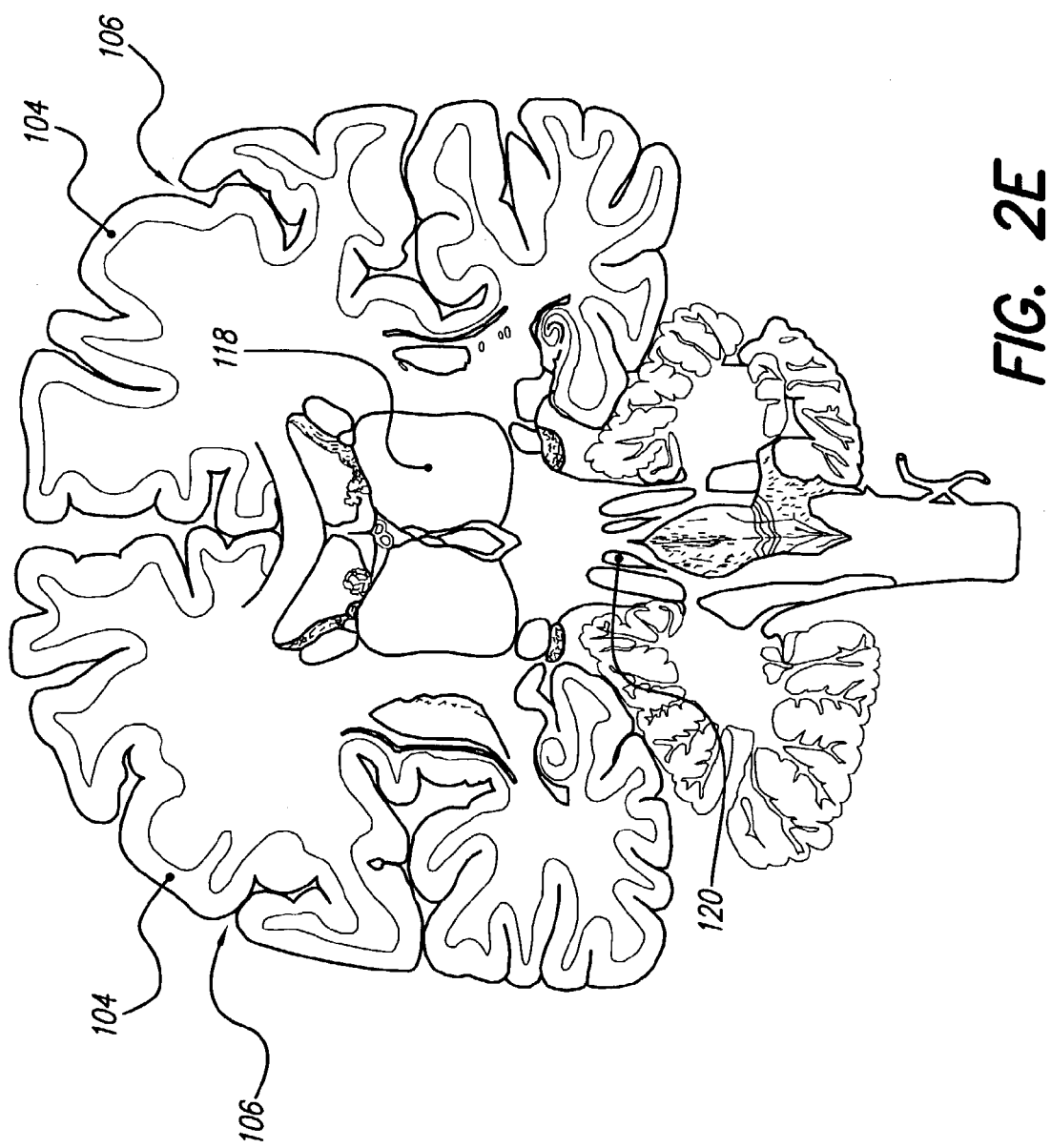
Figure 2F:
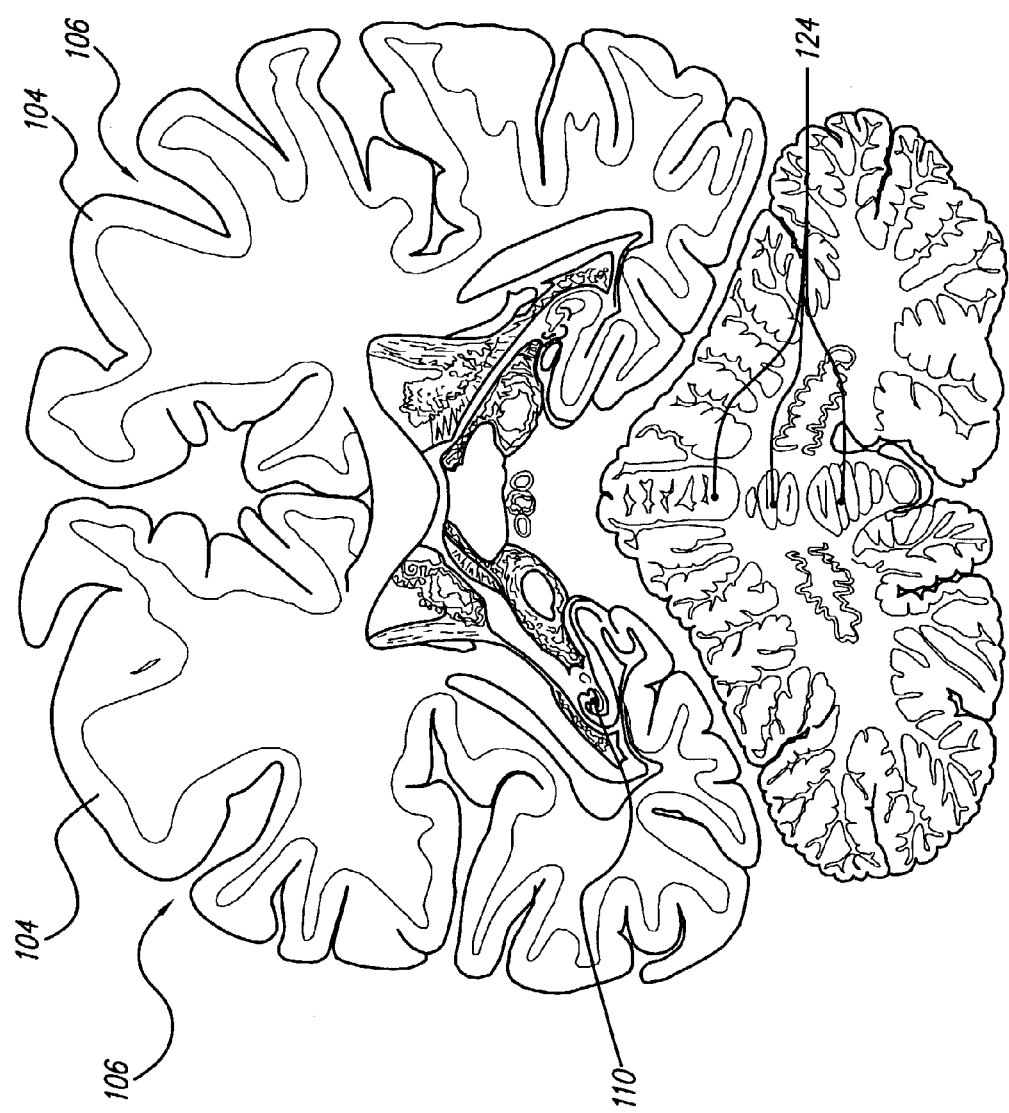

FIG. 1A depicts the dorsal surface of the brain stem, and FIGS. 1B and 1C are section views through the brain stem depicted in FIG. 1A, while FIG. 2A depicts the lateral surface of the brain, FIG. 2B depicts the medial surface of the head and FIGS. 2C–2F are coronal section views of the brain of FIG. 2B. FIG. 1B shows the location of the nucleus of the solitary tract (NTS) 100. FIG. 1C shows the principal (main) trigeminal sensory nucleus 102 and the spinal trigeminal nucleus 103. (The mesencephalic trigeminal nucleus 101 is not shown.) FIG. 2A shows the motor cortex 104 (which includes the precentral gyrus). As can be seen, motor cortex 104 lies on the outermost region of the brain, along the top and sides of the skull, and is the most posterior portion of the frontal lobe, lying just anterior to the central sulcus 106 (also known as the central fissure). The motor cortex 104 is also shown in FIG. 2C, as is the hippocampus 110. FIG. 2D shows the anterior nucleus 114 and the ventral lateral nucleus 116. The centromedian nucleus 118 and locus coeruleus 120 are shown in FIG. 2E. FIG. 2F shows the cerebellum, and again shows motor cortex 104, central sulcus 106, and hippocampus 110.

The present invention provides improved systems and methods for stimulating regions of the brain associated with epilepsy. Electrical and/or drug stimulation of such targets may provide therapeutic benefits in the management of epilepsy. Thus, via mechanisms described in more detail herein, the present invention provides electrical stimulation and/or a stimulating drug(s) to these areas to adjust the level of neural activity in these areas, and thereby treat epilepsy or prevent seizures.

For instance, the stimulation can decrease excitement of an area of the brain that demonstrates increased neural activity in epileptics relative to non-epileptic controls, such as a seizure focus, seizure foci, and/or the hippocampus, thereby treating epilepsy. The stimulation can decrease excitement of other areas of the brain theorized to benefit from inhibition, such as the NTS, thalamus (including centromedian, anterior, and ventrolateral nuclei), cerebellum, mesencephalic trigeminal nucleus, main trigeminal sensory nucleus, and spinal trigeminal nucleus. Relatively high-frequency electrical stimulation is likely to produce such inhibition. Infusion of stimulating drugs such as GABA or a GABA agonist (e.g., muscimol) may also produce this inhibitory effect.

On the other hand, the stimulation can increase excitement of an area of the brain that demonstrates decreased neural activity in epileptics relative to non-epileptic controls or that has been demonstrated to have a therapeutic effect(s) on epilepsy when neural activity of such area has been increased. Also, the stimulation can increase excitement of an area of the brain that has been demonstrated to lead to an increase in seizure frequency and seizure likelihood when lesioned or otherwise inhibited, such as the locus coeruleus. Relatively low-frequency electrical stimulation is likely to produce such excitation. Infusion of stimulating drugs such as a noradrenergic agonist may also produce this excitatory effect. As used herein, stimulate, stimulation, and stimulating refer to infusion of a stimulating drug(s) and/or supplying electrical current pulses. As such, infusion parameters and/or electrical current parameters are sometimes referred to herein as simply stimulation parameters, which parameters may include amplitude, volume, pulse width, infusion rate, and the like. Similarly, stimulation pulses may be pulses of electrical energy and/or pulses of drugs infused by various means and rates of infusion, such as intermittent infusion, infusion at a constant rate, and bolus infusion.

Herein, stimulating drugs comprise medications and other pharmaceutical compounds, anesthetic agents, synthetic or natural hormones, neurotransmitters, interleukins, cytokines, lymphokines, chemokines, growth factors, and other intracellular and intercellular chemical signals and messengers, and the like. Certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein may include stimulation of cell bodies and axons in the area.

In some alternatives, stimulation is provided by at least one system control unit (SCU) that is an implantable signal generator connected to an electrode(s) and/or an implantable pump connected to a catheter(s). These systems deliver electrical stimulation and/or one or more stimulating drugs to specific areas in the brain. One or more electrodes are surgically implanted in the brain to provide electrical stimulation, and/or one or more catheters are implanted in the brain to infuse the stimulating drug(s).

In various alternatives, stimulation is provided by one or more SCUs that are small, implantable stimulators, referred to herein as microstimulators. The microstimulators of the present invention may be similar to or of the type referred to as BION® devices (see FIGS. 3A, 3B, and 3C). The following documents describe various details associated with the manufacture, operation and use of BION implantable microstimulators, and are all incorporated herein by reference:

| Application/Patent/ Publication No. | Filing/Publication Date | Title |
| --- | --- | --- |
| U.S. Pat. No. 5,193,539 | Issued Mar. 16, 1993 | Implantable Microstimulator |
| U.S. Pat. No. 5,193,540 | Issued Mar. 16, 1993 | Structure and Method of Manufacture of an Implantable Microstimulator |
| U.S. Pat. No. 5,312,439 | Issued May 17, 1994 | Implantable Device Having an Electrolytic Storage Electrode |
| PCT Publication WO 98/37926 | Published Sep. 3, 1998 | Battery-Powered Patient Implantable Device |
| PCT Publication | Published | System of Implantable Devices For Monitoring and/or |

-continued

| Application/Patent/<br>Publication No. | Filing/Publication<br>Date | Title |
| --- | --- | --- |
| WO 98/43700<br>PCT Publication<br>WO 98/43701<br>U.S. Pat. No. 6,051,017 | Oct. 8, 1998<br>Published<br>Oct. 8, 1998<br>Issued<br>Apr. 18, 2000<br>Published<br>September, 1997 | Affecting Body Parameters<br>System of Implantable Devices For Monitoring and/or<br>Affecting Body Parameters<br>Improved Implantable Microstimulator and Systems<br>Employing Same<br>Micromodular Implants to Provide Electrical Stimulation<br>of Paralyzed Muscles and Limbs, by Cameron, et al.,<br>published in IEEE Transactions on Biomedical<br>Engineering, Vol. 44, No. 9, pages 781–790. |

Figure 3B:
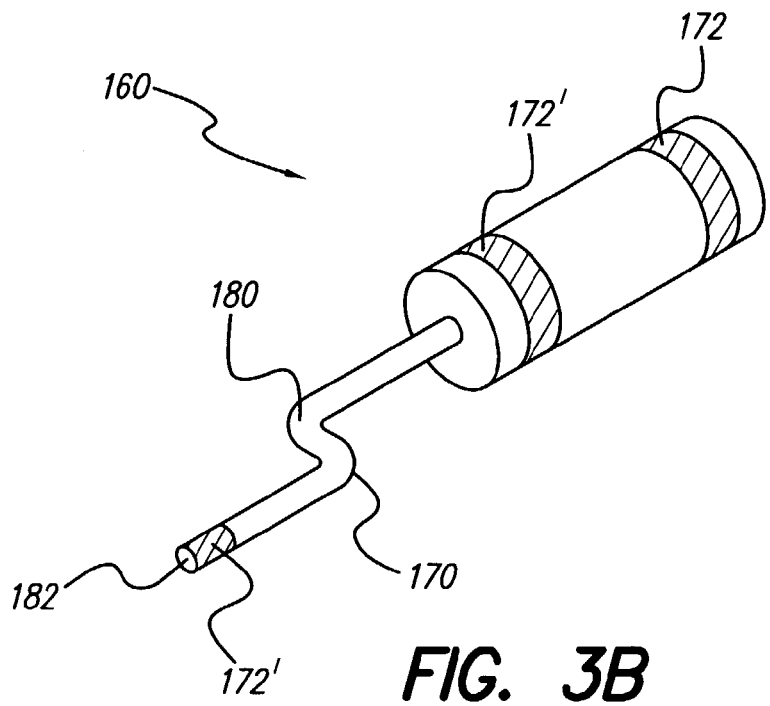
Figure 3C:
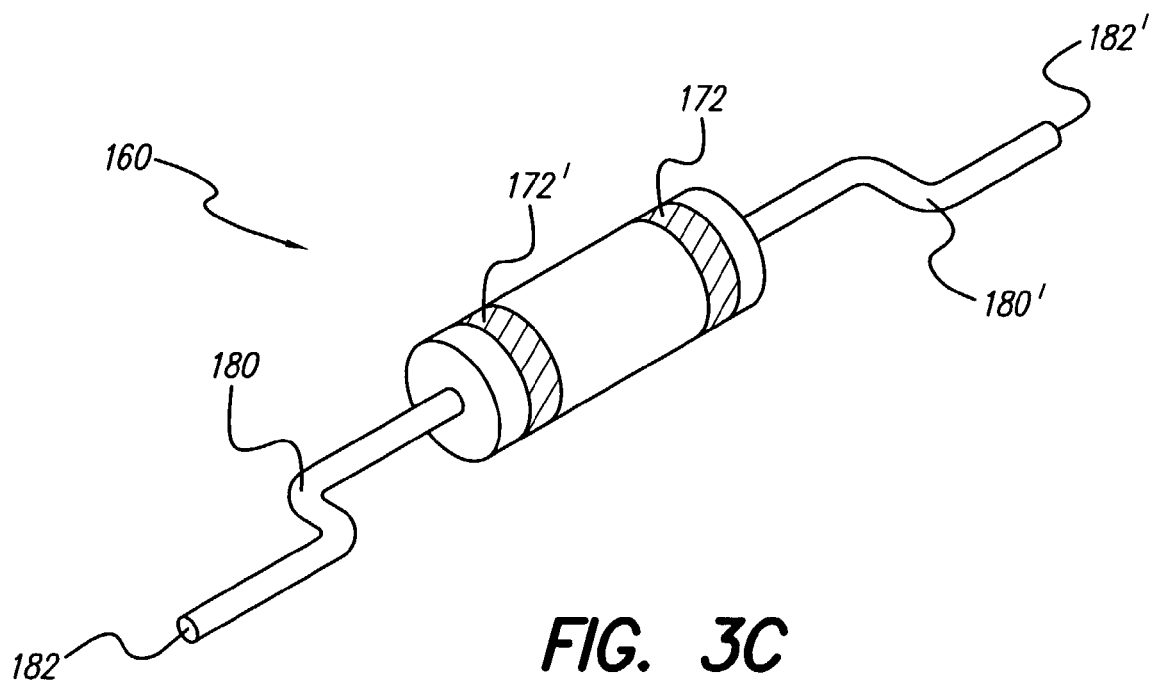

As shown in FIGS. 3A, 3B, and 3C, microstimulator SCUs 160 may include a narrow, elongated capsule 152 containing electronic circuitry 154 connected to electrodes 172 and 172', which may pass through the walls of the capsule at either end. Alternatively, electrodes 172 and/or 172' may be built into the case and/or arranged on a catheter 180 (FIG. 3B) or at the end of a lead, as described below. As detailed in the referenced publications, electrodes 172 and 172' generally comprise a stimulating electrode (to be placed close to the target) and an indifferent electrode (for completing the circuit). Other configurations of microstimulator SCU 160 are possible, as is evident from the above-referenced publications, and as described in more detail herein.

Certain configurations of implantable microstimulator SCU 160 are sufficiently small to permit placement in or adjacent to the structures to be stimulated. (As used herein, "adjacent" or "near" means as close as reasonably possible to targeted tissue, including touching or even being positioned within the tissue, but in general, may be as far as about 150 mm from the target tissue.) For instance, in these configurations, capsule 152 may have a diameter of about 4–5 mm, or only about 3 mm, or even less than about 3 mm. In these configurations, capsule length may be about 25–35 mm, or only about 20–25 mm, or even less than about 20 mm. The shape of the microstimulator may be determined by the structure of the desired target, the surrounding area, and the method of implantation. A thin, elongated cylinder with electrodes at the ends, as shown in FIGS. 3A, 3B, and 3C, is one possible configuration, but other shapes, such as cylinders, disks, spheres, and helical structures, are possible, as are additional electrodes, infusion outlets, leads, and/or catheters.

Microstimulator SCU 160, when certain configurations are used, may be implanted with a surgical tool such as a tool specially designed for the purpose, or with a hypodermic needle, or the like. Alternatively, microstimulator SCU 160 may be implanted via conventional surgical methods (e.g., via a small incision), or may be placed using endoscopic or laparoscopic techniques. A more complicated surgical procedure may be required for sufficient access to, for instance, the NTS 100, or for fixing the microstimulator in place.

Deep brain stimulation (DBS) electrodes are typically targeted and implanted with the guidance of a stereotactic frame. The diameter of the test or stimulation DBS electrodes is typically 1.5 mm or less. Microstimulator SCU 160 may be implanted with the aid of a stereotactic frame/tools via a minimal surgical procedure (e.g., through a small burr hole) adjacent to or in the sites mentioned above for the treatment of epilepsy, e.g., the NTS 100 or locus coeruleus 120, among other locations. As mentioned earlier, microstimulator SCU 160 may have a diameter of about 3 mm or less, allowing it to fit through a conventional burr hole in the skull. Instead of or in addition to stereotactic techniques, microstimulator SCU 160 may be implanted with the aid of other techniques, e.g., CT or ultrasound image guidance. However, even with such techniques, microstimulator SCU 160 itself requires only a relatively small hole in the skull for implantation, i.e., a hole as large as the diameter of the implanted device.

The external surfaces of microstimulator SCU 160 may advantageously be composed of biocompatible materials. Capsule 152 may be made of, for instance, glass, ceramic, or other material that provides a hermetic package that will exclude water vapor but permit passage of electromagnetic fields used to transmit data and/or power. Electrodes 172 and 172' may be made of a noble or refractory metal or compound, such as platinum, iridium, tantalum, titanium, titanium nitride, niobium or alloys of any of these, in order to avoid corrosion or electrolysis which could damage the surrounding tissues and the device.

In certain embodiments of the instant invention, microstimulator SCU 160 comprises two, leadless electrodes. However, either or both electrodes 172 and 172' may alternatively be located at the ends of short, flexible leads as described in U.S. patent application Ser. No. 09/624,130, filed Jul. 24, 2000, which is incorporated herein by reference in its entirety. The use of such leads permits, among other things, electrical stimulation to be directed more locally to targeted tissue(s) a short distance from the surgical fixation of the bulk of microstimulator SCU 160, while allowing most elements of the microstimulator to be located in a more surgically convenient site. This minimizes the distance traversed and the surgical planes crossed by the device and any lead(s). In most uses of this invention, the leads are no longer than about 150 mm.

As mentioned earlier, stimulation is provided in accordance with the teachings of the present invention by electrical stimulation and/or one or more stimulating drugs delivered to the body by one or more system control units (SCUs). In the case of electrical stimulation only, SCUs include a microstimulator and/or an implantable pulse/signal generator (IPG), or the like. In the case of drug infusion only, an SCU comprises an implantable pump or the like. In cases requiring both electrical stimulation and drug infusion, more than one SCU may be used. Alternatively, when needed and/or desired, an SCU provides both electrical stimulation and one or more stimulating drugs.

Figure 4:
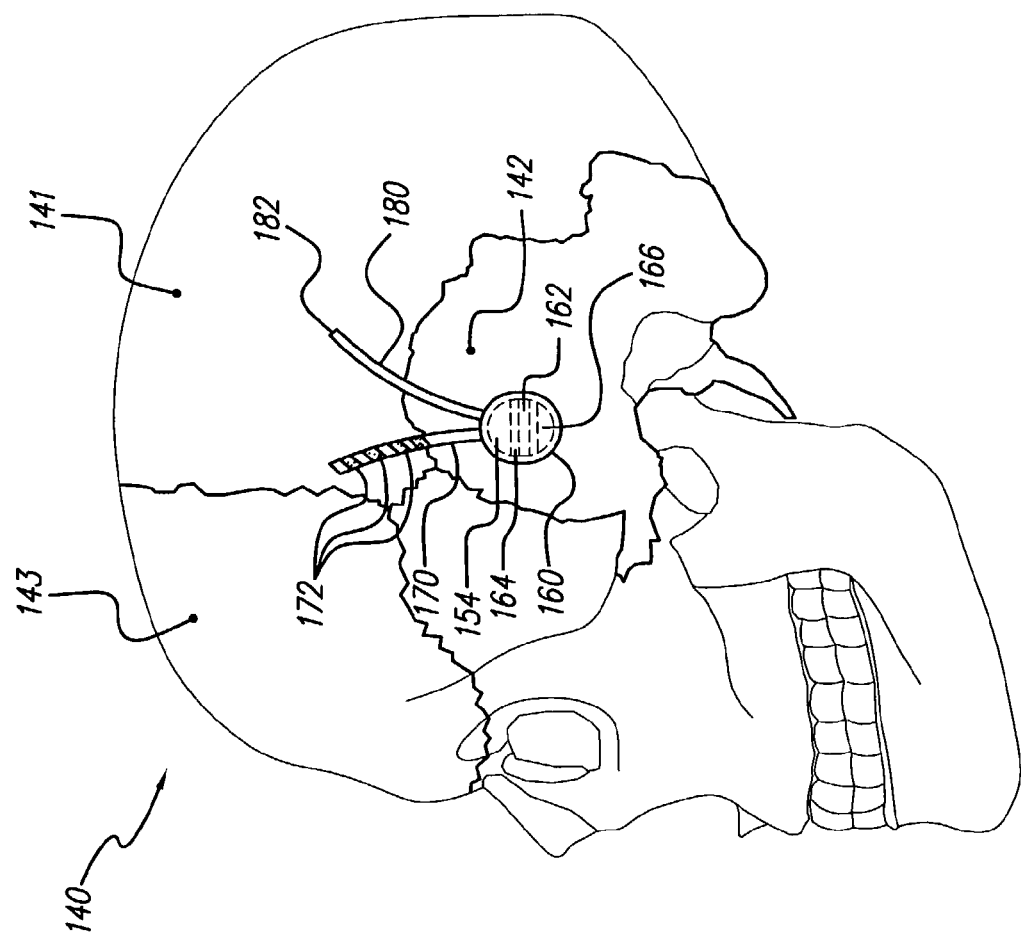
FIG. 4 illustrates a lateral view of the skull and components of some embodiments of the invention.

As depicted in FIG. 4, some embodiments of SCU 160 may be (but are not necessarily) implanted beneath the scalp, such as in a surgically-created shallow depression or opening in the skull 140, for instance, in parietal bone 141, temporal bone 142, or frontal bone 143. In several embodiments, SCU 160 conforms to the profile of surrounding tissue(s) and/or bone(s), and is small and compact. This may minimize pressure applied to the skin or scalp, which pressure may result in skin erosion or infection. In various embodiments, SCU 160 has a diameter of about 75 mm, or only about 65 mm, or even less than about 55 mm. In these configurations, SCU thickness may be approximately 10–12 mm, or even less than about 10 mm.

Figure 5:
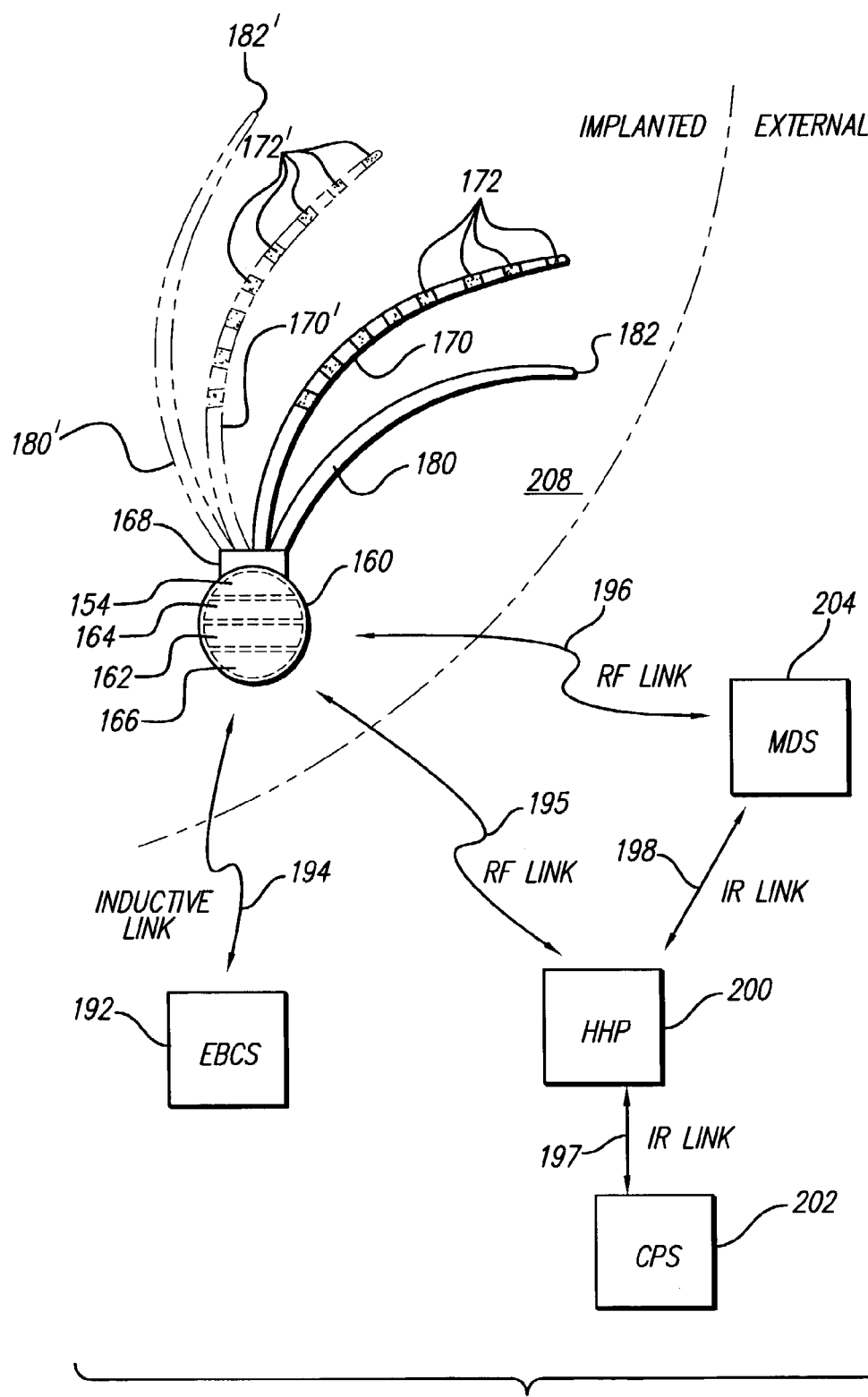
FIG. 5 illustrates internal and external components of certain embodiments of the invention.

As seen in the embodiments depicted in FIG. 5, one or more electrode leads 170 and/or catheters 180 attached to SCU 160 run subcutaneously, for instance, in a surgically-created shallow groove(s) in the skull, to an opening(s) in the skull, and pass through the opening(s) into or onto the brain parenchyma and surrounding tissue. Recessed placement of the SCU and the lead(s) and/or catheter(s) may decrease the likelihood of erosion of the overlying skin, and may minimize any cosmetic impact.

In embodiments such as in FIG. 5, electrode(s) 172 are carried on lead 170 having a proximal end coupled to SCU 160. The lead contains insulated wires electrically connecting electrodes 172 to SCU 160. SCU 160 contains electrical components 154 that produce electrical stimulation pulses that travel through the wires of lead 170 and are delivered to electrodes 172, and thus to the tissue surrounding electrodes 172. To protect the electrical components inside SCU 160, some or all of the case of the SCU may be hermetically sealed. For additional protection against, e.g., impact, the case may be made of metal (e.g. titanium) or ceramic, which materials are also, advantageously, biocompatible. In addition, SCU 160 may be configured to be Magnetic Resonance Imaging (MRI) compatible.

In some alternatives, the electrical stimulation may be provided as described in International Patent Application Serial Number PCT/US01/04417 (the '417 application), filed Feb. 12, 2001, and published Aug. 23, 2001 as WO 01/60450, which application is incorporated herein by reference in its entirety. As such, the electrical stimulation of the present invention may be as provided in this PCT application, which is directed to a "Deep Brain Stimulation System for the Treatment of Parkinson's Disease or Other Disorders".

In the case of treatment alternatively or additionally constituting drug infusion, SCU 160 (which herein refers to IPGs, implantable pumps, IPG/pump combinations, microstimulators for drug and/or electrical stimulation, and/or other alternative devices described herein) may contain at least one pump 162 for storing and dispensing one or more drugs through outlet(s) 182/182' and/or catheter(s) 180/180' into a predetermined site(s) in the brain tissue. When a catheter is used, it includes at least one infusion outlet 182, usually positioned at least at a distal end, while a proximal end of the catheter is connected to SCU 160.

According to some embodiments of the invention, such as described in the previously referenced '417 application and as depicted in FIG. 5, at least one lead 170 is attached to SCU 160, via a suitable connector 168, if necessary. Each lead includes at least one electrode 172, and may include as many as sixteen or more electrodes 172. Additional leads 170' and/or catheter(s) 180' may be attached to SCU 160. Hence, FIG. 5 shows (in phantom lines) a second catheter 180', and a second lead 170', having electrodes 172' thereon, also attached to SCU 160. Similarly, the SCUs 160 of FIGS. 3A, 3B, and 3C have outlets 182, 182' for infusing a stimulating drug(s) and electrodes 172, 172' for applying electrical stimulation.

Substantially cylindrical catheter(s) 180 and lead(s) 170 of certain embodiments of the present invention may be less than about 5 mm in diameter, or even less than about 1.5 mm in diameter. Electrodes 172, 172' on leads 170, 170' may be arranged as an array, for instance, as two or more collinear electrodes, or even as four or more collinear electrodes, or they may not be collinear. A tip electrode may also be supplied at the distal end of one or more leads. Alternatively, the electrodes may be arranged on a catheter 180/180', which catheter may have a diameter of about 2–3 mm or less, for example. The SCU may thus produce electrical stimulation through the electrodes and infuse one or more stimulating drugs through the catheter.

In some embodiments, SCU 160 is programmable to produce either monopolar electrical stimulation, e.g., using the SCU case as an indifferent electrode, or bipolar electrical stimulation, e.g., using one of the electrodes of the electrode array as an indifferent electrode. Some embodiments of SCU 160 have at least four channels and drive up to sixteen electrodes or more.

SCU 160 contains, when necessary and/or desired, electronic circuitry 154 for receiving data and/or power from outside the body by inductive, radio frequency (RF), or other electromagnetic coupling. In some embodiments, electronic circuitry 154 includes an inductive coil for receiving and transmitting RF data and/or power, an integrated circuit (IC) chip for decoding and storing stimulation parameters and generating stimulation pulses (either intermittent or continuous), and additional discrete electronic components required to complete the electronic circuit functions, e.g. capacitor(s), resistor(s), coil(s), and the like.

SCU 160 also includes, when necessary and/or desired, a programmable memory 164 for storing a set(s) of data, stimulation, and control parameters. Among other things, memory 164 may allow electrical and/or drug stimulation to be adjusted to settings that are safe and efficacious with minimal discomfort for each individual. Specific parameters may provide therapeutic advantages for various types of epilepsy. For instance, some patients may respond favorably to intermittent stimulation, while others may require continuous treatment for relief. In some embodiments, electrical and drug stimulation parameters are controlled independently, e.g., continuous electrical stimulation and no drug stimulation. However, in some instances, they may advantageously be coupled, e.g., electrical stimulation may be programmed to occur only during drug infusion.

In addition, different stimulation parameters may have different effects on neural tissue. Therefore, parameters may be chosen to target specific neural populations and/or to exclude others, or to increase neural activity in specific neural populations and/or to decrease neural activity in others. For example, relatively low frequency neurostimulation (i.e., less than about 100–150 Hz) typically has an excitatory effect on surrounding neural tissue, leading to increased neural activity, whereas relatively high frequency neurostimulation (i.e., greater than about 100–150 Hz) may have an inhibitory effect, leading to decreased neural activity. Similarly, excitatory neurotransmitters (e.g., glutamate, dopamine, norepinephrine, epinephrine, acetylcholine, serotonin), agonists thereof (e.g., glutamate receptor agonists such as N-methyl-D-aspartate (NMDA), alpha-amino-3-hydroxy-5-methylisoxazole-4-propionate (AMPA), and kainate), and agents that act to increase levels of an excitatory neurotransmitter(s) (e.g., edrophonium, Mestinon) generally have an excitatory effect on neural tissue, while inhibitory neurotransmitters (e.g., dopamine, glycine, and gamma-aminobutyric acid, a.k.a. GABA), agonists thereof (e.g., muscimol), and agents that act to increase levels of an inhibitory neurotransmitter(s) generally have an inhibitory effect. (Dopamine acts as an excitatory neurotransmitter in some locations and circumstances, and as an inhibitory neurotransmitter in other locations and circumstances.) However, antagonists of inhibitory neurotransmitters (e.g., bicuculline) and agents that act to decrease levels of an inhibitory neurotransmitter(s) have been demonstrated to excite neural tissue, leading to increased neural activity. Similarly, excitatory neurotransmitter antagonists (e.g. prazosin, metoprolol) and agents that decrease levels of an excitatory neurotransmitter(s) (e.g., acetylcholinesterase) may inhibit neural activity.

Some embodiments of SCU 160 also include a power source and/or power storage device 166. Possible power options for a stimulation device of the present invention, described in more detail below, include but are not limited to an external power source coupled to the stimulation device, e.g., via an RF link, a self-contained power source utilizing any suitable means of generation or storage of energy (e.g., a primary battery, a replenishable or rechargeable battery such as a lithium ion battery, an electrolytic capacitor, a super- or ultra-capacitor, or the like), and if the self-contained power source is replenishable or rechargeable, means of replenishing or recharging the power source (e.g., an RF link, an optical link, a thermal link, or other energy-coupling link).

In embodiments such as shown in FIG. 5, SCU 160 includes a rechargeable battery as a power source/storage device 166. The battery is recharged, as required, from an external battery charging system (EBCS) 192, typically through an inductive link 194. In these embodiments, and as explained more fully in the earlier referenced '417 PCT application, SCU 160 includes a processor and other electronic circuitry 154 that allow it to generate stimulation pulses that are applied to a patient 208 through electrodes 172 and/or outlet(s) 182 in accordance with a program and stimulation parameters stored in programmable memory 164. Stimulation pulses of drugs include various types and/or rates of infusion, such as intermittent infusion, infusion at a constant rate, and bolus infusion.

According to certain embodiments of the invention, an SCU operates independently. According to various embodiments of the invention, an SCU operates in a coordinated manner with other SCU(s), other implanted device(s), and/or other device(s) external to the patient's body. For instance, an SCU may control or operate under the control of another implanted SCU(s), other implanted device(s), and/or other device(s) external to the patient's body. An SCU may communicate with other implanted SCUs, other implanted devices, and/or devices external to a patient's body via, e.g., an RF link, an ultrasonic link, a thermal link, and/or an optical link. Specifically, an SCU may communicate with an external remote control (e.g., patient and/or physician programmer) that is capable of sending commands and/or data to an SCU and that may also be capable of receiving commands and/or data from an SCU.

For example, some embodiments of SCU 160 of the present invention may be activated and deactivated, programmed and tested through a hand held programmer (HHP) 200 (which may also be referred to as a patient programmer and may be, but is not necessarily, hand held), a clinician programming system (CPS) 202 (which may also be hand held), and/or a manufacturing and diagnostic system (MDS) 204 (which may also be hand held). HHP 200 may be coupled to SCU 160 via an RF link 195. Similarly, MDS 204 may be coupled to SCU 160 via another RF link 196. In a like manner, CPS 202 may be coupled to HHP 200 via an infra-red link 197; and MDS 204 may be coupled to HHP 200 via another infra-red link 198. Other types of telecommunicative links, other than RF or infra-red may also be used for this purpose. Through these links, CPS 202, for example, may be coupled through HHP 200 to SCU 160 for programming or diagnostic purposes. MDS 204 may also be coupled to SCU 160, either directly through RF link 196, or indirectly through IR link 198, HHP 200, and RF link 195.

Figure 6:
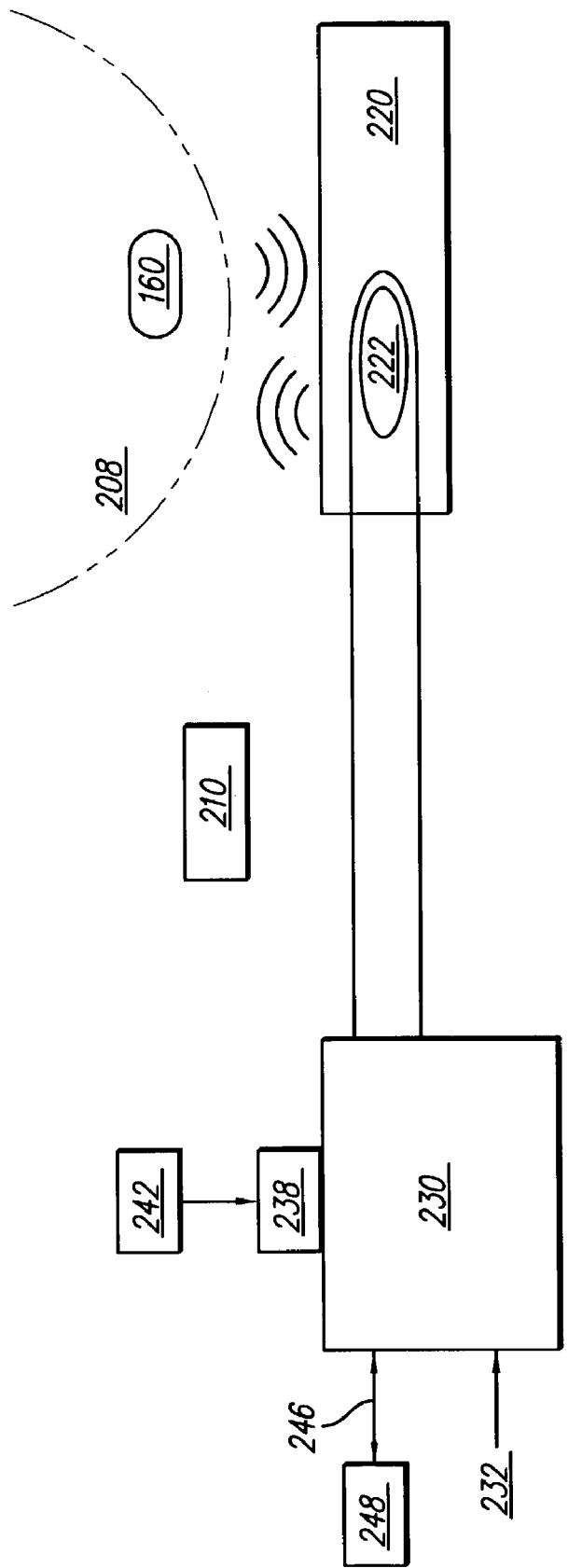
FIG. 6 illustrates external components of various embodiments of the invention.

In certain embodiments, using for example, a BION microstimulator(s) as described in the above referenced publications, and as illustrated in FIG. 6, the patient 208 switches SCU 160 on and off by use of controller 210, which may be handheld. SCU 160 is operated by controller 210 by any of various means, including sensing the proximity of a permanent magnet located in controller 210, sensing RF transmissions from controller 210, or the like.

External components for programming and/or providing power to various embodiments of SCU 160 are also illustrated in FIG. 6. When communication with such an SCU 160 is desired, patient 208 is positioned on or near external appliance 220, which appliance contains one or more inductive coils 222 or other means of communication (e.g., RF transmitter and receiver). External appliance 220 is connected to or is a part of external electronic circuitry appliance 230 which may receive power 232 from a conventional power source. External appliance 230 contains manual input means 238, e.g., a keypad, whereby the patient 208 or a caregiver 242 may request changes in electrical and/or drug stimulation parameters produced during the normal operation of SCU 160. In these embodiments, manual input means 238 includes various electromechanical switches and/or visual display devices that provide the patient and/or caregiver with information about the status and prior programming of SCU 160.

Alternatively or additionally, external electronic appliance 230 is provided with an electronic interface means 246 for interacting with other computing means 248, such as by a serial interface cable or infrared link to a personal computer or to a telephone modem or the like. Such interface means 246 may permit a clinician to monitor the status of the implant and prescribe new stimulation parameters from a remote location.

The external appliance(s) may be embedded in a cushion, pillow, hat, or the like. Other possibilities exist, including a head band, patch, or other structure(s) that may be affixed to the patient's body or clothing. External appliances may include a package that can be, e.g., worn on the belt, may include an extension to a transmission coil affixed, e.g., with a Velcro® band or an adhesive, or may be combinations of these or other structures able to perform the functions described herein.

In the present invention, it is not necessary or preferable to include a sensing function or device, in which case stimulation parameters are determined and refined, for instance, by patient feedback, or the like. In alternate embodiments, a patient's response to and/or need for treatment may be sensed and used to help determine the strength and/or duration of electrical stimulation and/or the amount and/or type(s) of stimulating drug(s) required to produce the desired effect. For example electrical activity of the brain (e.g., EEG or discharge frequency of a neural population), muscle activity (e.g., limb EMG), or other activity may be sensed. For instance, one or more electrodes may be used for recording electrical signals from the brain.

Thus, it is seen that in accordance with the present invention, one or more external appliances may be provided to interact with SCU 160, and may be used to accomplish, potentially among other things, one or more of the following functions:

Function 1: If necessary, transmit electrical power from the external electronic appliance 230 via appliance 220 to SCU 160 in order to power the device and/or recharge the power source/storage device 166.

Function 2: Transmit data from the external appliance 230 via the external appliance 220 to SCU 160 in order to change the parameters of electrical and/or drug stimulation used by SCU 160.

Function 3: Transmit data indicating state of the SCU 160 (e.g., battery level, drug level, stimulation parameters, etc.) to external appliance 230 via external appliance 220.

Additional functions may include sensing and adjustment of electrical and/or drug stimulation parameters based on the sensed information.

By way of example, a treatment modality for epilepsy may be carried out according to the following sequence of procedures:

1. An SCU 160 is implanted so that its electrodes 172 and/or infusion outlet 182 are located in or on or near the NTS 100. If necessary or desired, electrodes 172' and/or infusion outlets 182' may additionally or alternatively be located in or on or near a seizure focus.

2. Using Function 2 described above (i.e., transmitting data) of external electronic appliance 230 and external appliance 220, SCU 160 is commanded to produce a series of inhibitory electrical stimulation pulses, possibly with gradually increasing amplitude, and possibly while infusing gradually increasing amounts of an inhibitory neurotransmitter or an agonist thereof, e.g., GABA or GABA agonist such as muscimol.

3. From patient or other assessment (e.g., clinician observation, such as EEG monitored during programming), the stimulus threshold for obtaining a response is determined and is used by a clinician 242 acting directly 238 or by other computing means 248 to transmit the desired electrical and/or drug stimulation parameters to SCU 160 in accordance with Function 2.

4. When patient 208 desires to invoke electrical stimulation and/or drug infusion, patient 208 employs controller 210 to set SCU 160 in a state where it delivers a prescribed stimulation pattern from a predetermined range of allowable stimulation patterns.

5. To cease electrical and/or drug stimulation, patient 208 employs controller 210 to turn off SCU 160.

6. Periodically, the patient or caregiver recharges the power source/storage device 166 of SCU 160, if necessary, in accordance with Function 1 described above (i.e., transmit electrical power).

As an additional example, another treatment modality for epilepsy may be carried out according to the following sequence of procedures:

1. An SCU 160 is implanted so that its electrodes 172 and/or infusion outlet 182 are located in or on or near the main trigeminal sensory nucleus 102. If necessary or desired, electrodes 172' and/or infusion outlets 182' may additionally or alternatively be located in or on or near a seizure focus.

2. Using Function 2 described above (i.e., transmitting data) of external electronic appliance 230 and external appliance 220, SCU 160 is commanded to produce a series of inhibitory electrical stimulation pulses, possibly with gradually increasing amplitude, and possibly while infusing gradually increasing amounts of an inhibitory neurotransmitter or an agonist thereof, e.g., GABA or GABA agonist such as muscimol.

3. From patient or other assessment (e.g., clinician observation, such as EEG monitored during programming), the stimulus threshold for obtaining a response is determined and is used by a clinician 242 acting directly 238 or by other computing means 248 to transmit the desired electrical and/or drug stimulation parameters to SCU 160 in accordance with Function 2.

4. When patient 208 desires to invoke electrical stimulation and/or drug infusion, patient 208 employs controller 210 to set SCU 160 in a state where it delivers a prescribed stimulation pattern from a predetermined range of allowable stimulation patterns.

5. To cease electrical and/or drug stimulation, patient 208 employs controller 210 to turn off SCU 160.

6. Periodically, the patient or caregiver recharges the power source/storage device 166 of SCU 160, if necessary, in accordance with Function 1 described above (i.e., transmit electrical power).

For the treatment of any of the various types of epilepsy, it may be desirable to modify or adjust the algorithmic functions performed by the implanted and/or external components, as well as the surgical approaches, in ways that would be obvious to skilled practitioners of these arts. For example, in some situations, it may be desirable to employ more than one SCU 160, each of which could be separately controlled by means of a digital address. Multiple channels and/or multiple patterns of electrical and/or drug stimulation might thereby be programmed by the clinician and controlled by the patient in order to, for instance, deal with complex or multiple symptoms or conditions, such as temporal lobe epilepsy attributed to bilateral mesial temporal sclerosis.

Figure 7:
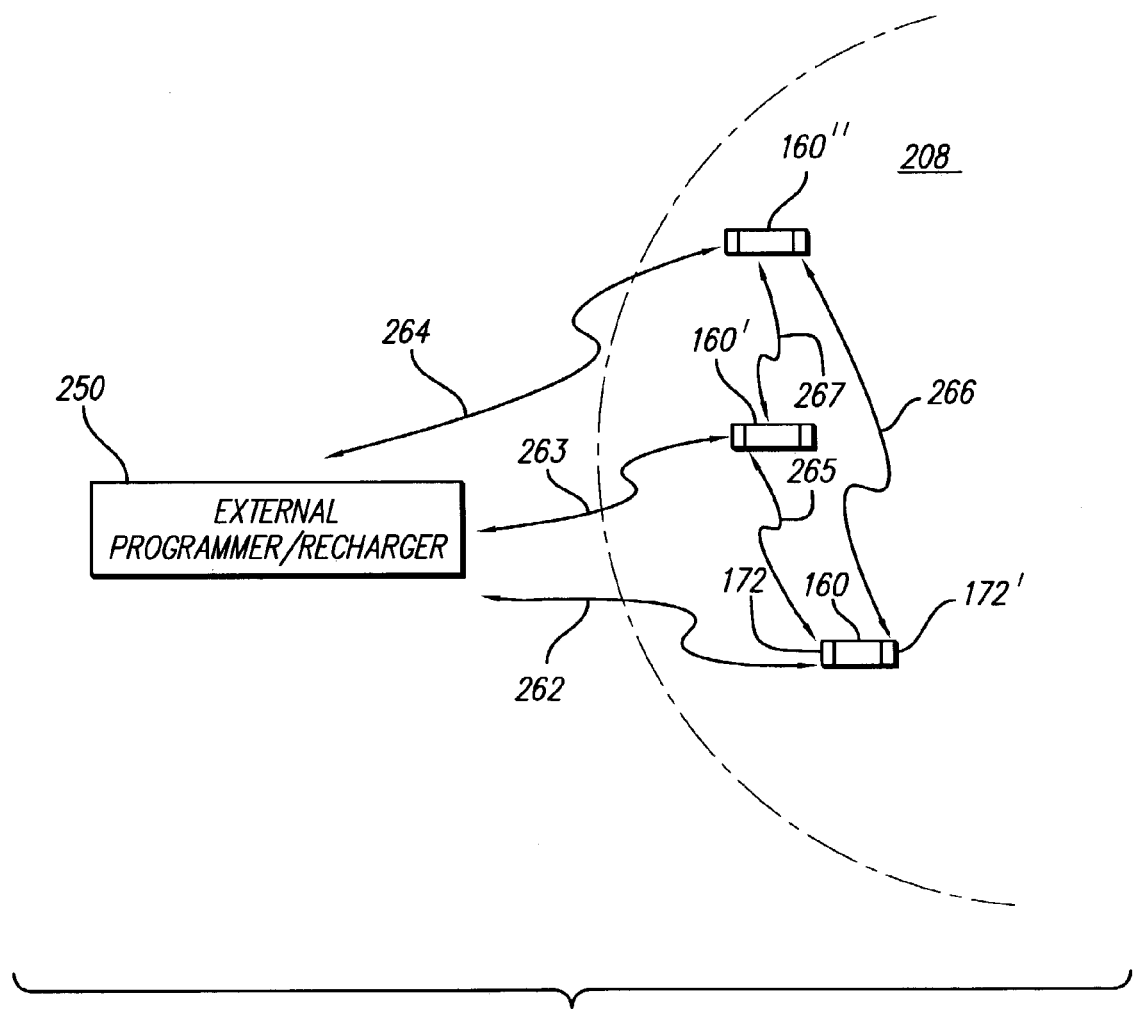
FIG. 7 depicts a system of implantable devices that communicate with each other and/or with external control/programming devices.

For instance, as shown in the example of FIG. 7, a first SCU 160, implanted beneath the skin of the patient 208, provides a first medication or substance; a second SCU 160' provides a second medication or substance; and a third SCU 160" provides electrical stimulation via electrodes 172 and 172'. As mentioned earlier, the implanted devices may operate independently or may operate in a coordinated manner with other similar implanted devices, other implanted devices, or other devices external to the patient's body, as shown by the control lines 262, 263, 264, 265, 266, and 267 in FIG. 7. That is, in accordance with certain embodiments of the invention, the external controller 250 controls the operation of each of the implanted devices 160, 160' and 160". According to various embodiments of the invention, an implanted device, e.g. SCU 160, may control or operate under the control of another implanted device(s), e.g. SCU 160' and/or SCU 160". That is, a device made in accordance with the invention may communicate with other implanted stimulators, other implanted devices, and/or devices external to a patient's body, e.g., via an RF link, an ultrasonic link, a thermal link, an optical link, or the like. Specifically, as illustrated in FIG. 7, SCU 160, 160', and/or 160", made in accordance with the invention, may communicate with an external remote control (e.g., patient and/or physician programmer 250) that is capable of sending commands and/or data to implanted devices and that may also be capable of receiving commands and/or data from implanted devices.

However, according to a preferred embodiment of the present invention, SCU 160 incorporates no means for sensing, which allows it to maintains its simplicity and thus its small size. The small size to SCU 160 advantageously allows it to be implanted entirely in the skull and/or brain. In addition, since SCU 160 preferably operates in an open-loop (i.e., without automated adjustments based on feedback), a significant amount of programming is avoided. The relatively modest control parameter set for SCU 160 allows for rapid programming, which programming is done manually.

According to some embodiments of the invention, the electrical and/or drug stimulation decreases activity of one or more areas of the brain that exhibit chronic increased activity, relative to control subjects, in patients experiencing epilepsy. These areas may include a seizure focus, seizure foci, and/or the hippocampus. In addition, the stimulation can decrease excitement of an area of the brain theorized to benefit from inhibition, such as the NTS, thalamus (including centromedian, anterior, and ventrolateral nuclei), cerebellum, mesencephalic trigeminal nucleus, main trigeminal sensory nucleus, and spinal trigeminal nucleus. Such inhibitory stimulation is likely to be produced by relatively high-frequency electrical stimulation (e.g., greater than about 100–150 Hz), an excitatory neurotransmitter antagonist(s) (e.g. prazosin, metoprolol), an inhibitory neurotransmitter(s) (e.g., GABA), an agonist thereof, an agent that increases the level of an inhibitory neurotransmitter, an agent that decreases the level of an excitatory neurotransmitter, a local anesthetic agent (e.g., lidocaine), and/or an analgesic medication.

According to other embodiments of the invention, the electrical and/or drug stimulation increases activity of one or more areas of the brain that exhibit chronic decreased activity, relative to control subjects, in patients experiencing epilepsy, thereby treating or preventing such disorder and/or the symptoms and/or pathological consequences thereof. In addition, the stimulation can increase excitement of an area of the brain that has been demonstrated to have a therapeutic effect(s) on epilepsy when neural activity of such area has been increased. Also, the stimulation can increase excitement of an area of the brain that has been demonstrated to lead to an increase in seizure frequency and seizure likelihood when lesioned or otherwise inhibited, such as the locus coeruleus. Such excitatory stimulation is likely to be produced by relatively low-frequency electrical stimulation (e.g., less than about 100–150 Hz), an excitatory neurotransmitter (e.g., glutamate, norepinephrine), an excitatory cortical neurotransmitter agonist (e.g., bethanechol, glutamate receptor agonist such as NMDA, norepinephrine agonist such as phenylephrine), an inhibitory neurotransmitter antagonist(s) (e.g., bicuculline), an agent that increases the level of an excitatory neurotransmitter (e.g., edrophonium), and/or an agent that decreases the level of an inhibitory neurotransmitter.

In various embodiments, communication means described earlier may be used to orchestrate first the activation of SCU(s) targeting an area(s) of the brain, and then, when appropriate, SCU(s) targeting another area(s) and/or by different means. This orchestration would preferably be programmed manually, and not based on a sensed condition. Alternatively, the orchestration may be based on sensed information, as described earlier.

While the invention herein disclosed has been described by means of specific embodiments and applications thereof, numerous modifications and variations could be made thereto by those skilled in the art without departing from the scope of the invention set forth in the claims.

What is claimed is:

1. A method of treating a patient with epilepsy, comprising:
    implanting at least one system control unit entirely within the brain of the patient, wherein the at least one unit controls the delivery of at least one stimulus to at least one area of the brain affecting epilepsy;
    applying the at least one stimulus to the at least one area of the brain in order to at least in part alleviate the epilepsy of the patient being treated; and
    applying the at least one stimulus to decrease activity of at least one of the main trigeminal sensory nucleus, the spinal trigeminal nucleus, and the mesencephalic trigeminal nucleus;
    wherein the at least one system control unit is a microstimulator implanted entirely within the brain.

2. The method of claim 1 wherein the system control unit is connected to at least one electrode, and wherein the stimulus comprises electrical stimulation delivered via the at least one electrode.

3. The method of claim 1 wherein the system control unit is connected to at least one infusion outlet, and wherein the stimulus comprises stimulation via one or more drugs delivered through the at least one outlet.

4. The method of claim 1 wherein the system control unit is connected to at least one electrode and to at least one infusion outlet, and wherein the stimulus comprises both electrical stimulation delivered via the at least one electrode and stimulation via one or more drugs delivered through the at least one outlet.

5. The method of claim 1 wherein the stimulating pulses are at least relatively high-frequency electrical pulses applied at greater than about 100–150 Hz.

6. The method of claim 1 wherein the stimulating pulses are at least infusion pulses of at least one of an inhibitory neurotransmitter, an inhibitory neurotransmitter agonist, an agent that increases the level of an inhibitory neurotransmitter, an excitatory neurotransmitter antagonist, an agent that decreases the level of an excitatory neurotransmitter, a local anesthetic agent, and an analgesic medication.

7. The method of claim 6 wherein the infusion pulses are pulses of at least one of dopamine, glycine, and gamma-aminobutyric acid, muscimol, prazosin, metoprolol, acetylcholinesterase, bicuculline methiodide, and lidocaine.

8. The method of claim 1 further comprising sensing at least one condition and using the at least one sensed condition to automatically determine the stimulating pulses to apply.

9. The method of claim 1 wherein the at least one system control unit is programmed manually.

10. A method of treating a patient with epilepsy, comprising:
    providing at least one system control unit that generates stimulating pulses in accordance with prescribed parameters, which stimulating pulses are at least one of infusion pulses and electrical stimulation pulses;
    providing, connected to the at least one system control unit, at least one catheter with at least one discharge portion or at least one lead with at least one electrode;
    implanting at least one of the at least one discharge portion and the at least one electrode adjacent to at least one brain structure affecting epilepsy;
    implanting the at least one system control unit in the patient, wherein the at least one unit controls the delivery of the stimulating pulses applied to the at least one brain structure to be stimulated;
    tunneling at least one of the at least one catheter and the at least one lead between the at least one brain structure and the system control unit location;
    applying the stimulating pulses to decrease activity of the at least one brain structure in order to at least in part alleviate the epilepsy of the patient being treated; and wherein the at least one brain structure is at least the nucleus of tractus solitarius (NTS).

11. The method of claim 10 wherein the stimulating pulses are at least relatively high-frequency electrical pulses applied at greater than about 100–150 Hz.

12. The method of claim 10 wherein the stimulating pulses are at least infusion pulses of at least one of an inhibitory neurotransmitter, an inhibitory neurotransmitter agonist, an agent that increases the level of an inhibitory neurotransmitter, an excitatory neurotransmitter antagonist, an agent that decreases the level of an excitatory neurotransmitter, a local anesthetic agent, and an analgesic medication.

13. The method of claim 12 wherein the infusion pulses are pulses of at least one of dopamine, glycine, and gamma-aminobutyric acid, muscimol, prazosin, metoprolol, acetylcholinesterase, bicuculline methiodide, and lidocaine.

14. The method of claim 10 further comprising sensing at least one condition and using the at least one sensed condition to automatically determine the stimulating pulses to apply.

15. The method of claim 10 wherein the at least one system control unit is programmed manually.

16. A method of treating a patient with epilepsy, comprising the steps of:
    providing at least one system control unit that generates stimulating pulses in accordance with prescribed parameters, which stimulating pulses are at least one of infusion pulses and electrical stimulation pulses;
    providing, connected to the at least one system control unit, at least one catheter with at least one discharge portion or at least one lead with at least one electrode;
    implanting at least one of the at least one discharge portion and the at least one electrode adjacent to at least one brain structure affecting epilepsy;
    implanting the at least one system control unit in the patient, wherein the at least one unit controls the delivery of the stimulating pulses applied to the at least one brain structure to be stimulated;
    tunneling at least one of the at least one catheter and the at least one lead between the at least one brain structure and the system control unit location;
    applying the stimulating pulses to decrease activity of the at least one brain structure in order to at least in part alleviate the epilepsy of the patient being treated; and
    wherein the at least one brain structure is at least the nucleus of tractus solitarius (NTS).

17. The method of claim 16 wherein the stimulating pulses are at least relatively high-frequency electrical pulses applied at greater than about 100–150 Hz.

18. The method of claim 16 wherein the stimulating pulses are at least infusion pulses of at least one of an inhibitory neurotransmitter, an inhibitory neurotransmitter agonist, an agent that increases the level of an inhibitory neurotransmitter, an excitatory neurotransmitter antagonist, an agent that decreases the level of an excitatory neurotransmitter, a local anesthetic agent, and an analgesic medication.

19. The method of claim 18 wherein the infusion pulses are pulses of at least one of dopamine, glycine, and gamma-aminobutyric acid, muscimol, prazosin, metoprolol, acetylcholinesterase, bicuculline methiodide, and lidocaine.

* * * * *